United States Patent [19]

Shetty

[11] 4,233,217
[45] Nov. 11, 1980

[54] SUBSTITUTED 1,2,4,5-TETRAHYDRO-3H, 3 BENZAZEPINES

[75] Inventor: Bola V. Shetty, Rockville, Md.

[73] Assignee: Pennwalt Corporation, Philadelphia, Pa.

[21] Appl. No.: 41,575

[22] Filed: May 21, 1979

Related U.S. Application Data

[60] Division of Ser. No. 747,151, Dec. 3, 1976, abandoned, which is a continuation of Ser. No. 523,092, Nov. 12, 1974, abandoned, which is a continuation-in-part of Ser. No. 241,091, Apr. 4, 1972, abandoned, which is a continuation of Ser. No. 711,897, Mar. 11, 1968, abandoned.

[51] Int. Cl.³ .................. A61K 31/55; C07D 223/16
[52] U.S. Cl. .................. 260/239 BB; 260/243.3;
260/244.4; 260/326 N; 260/330.3; 260/347.7;
260/347.8; 542/400; 542/429; 542/468;
542/469; 424/244
[58] Field of Search .................. 260/239 BB

[56] References Cited

U.S. PATENT DOCUMENTS 2,520,264  8/1950  Walter .................. 260/239 BB
3,242,164  3/1966  Sherlock .................. 260/239 BB Primary Examiner—Alton D. Hollins

[57] ABSTRACT

Compounds of the general formula:

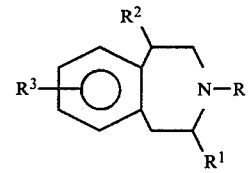

and pharmaceutical acceptable salts thereof wherein

R is H, lower alkyl, lower alkenyl, lower aralkenyl, cycloalkyl-alkyl, propargyl, lower aralkyl, hydroxyalkyl and esters thereof, heterocyclic, heterocyclic-alkyl, alkyl-aminoalkyl, adamantylalkyl, aralkyl-heterocyclic-alkyl and alkyl-aralkyl-heterocyclic alkyl;

$R^1$ is H, lower alkyl, phenyl, or phenylloweralkyl;
$R^2$ is hydrogen or lower alkyl;
$R^3$ is hydrogen; lower alkoxy; lower alkoxy alkyl ether of hydroxy; amino; lower alkyl; halogen; nitro; hydroxy; or carboxylic acid ester of hydroxy group, which compounds are useful as analgesics, narcotic antagonists and antihistaminics.

2 Claims, No Drawings

SUBSTITUTED 1,2,4,5-TETRAHYDRO-3H, 3 BENZAZEPINES

This is a division of application Ser. No. 747,151, filed Dec. 3, 1976, abandoned, which in turn is a continuation of application Ser. No. 523,092, filed Nov. 12, 1974, abandoned, which in turn is a continuation-in-part of application Ser. No. 241,091 filed Apr. 4, 1972, abandoned, which in turn is a Continuation of Application Ser. No. 711,897 filed Mar. 11, 1968, abandoned.

This invention relates to substituted 1,2,4,5-tetrahydro-3H,3-benzazepines that are useful as agents for producing analgesia and as antagonists of narcotics such as morphine.

The compounds of this invention have the general formula:

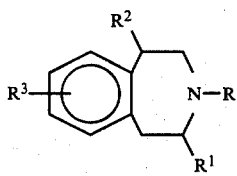

wherein

R is hydrogen; lower alkyl containing 1 to 6 carbon atoms; lower alkenyl containing 3 to 6 carbon atoms, e.g. $-CH_2-CH=CH_2$, $-CH_2-CH=CH-CH_3$, $-CH_2-C(CH_3)=CH_2$, $-CH_2-CH=C(CH_3)_2$ and the like; lower aralkenyl (9 to 12 carbons), e.g. phenylallyl; cycloalkyl alkyl (4 to 12 carbons), e.g. cyclopropylmethyl, cyclobutylmethyl, cyclopentylmethyl and the like; propargyl; lower aralkyl (7 to 12 carbons), the aryl group being from the group consisting of phenyl, tolyl, nitrophenyl, methoxyphenyl, hydroxyphenyl, the phenyl compound being substituted in the ortho, meta or para position; hydroxyalkyl, a lower alkyl ester of hydroxyalkyl; heterocyclic such as thienyl, pyridinyl, furyl; heterocyclic alkyl such as phenylpiperazinylethyl, 4-hydroxy-4-phenyl-1-piperidinylethyl, thienylethyl, piperidinylethyl, phenylpiperidinylethyl, piperazinylethyl; morpholinylethyl, 2-phthalimidoethyl- (the phenyl moiety may be substituted in the o, m, or p- position with $NH_2$, OH, $OCH_3$, halogen, alkyl), 2-(2-isoindolinyl)-ethyl- (the phenyl moiety may be substituted in the o, m, or p- position with $NH_2$, OH, $OCH_3$, halogen, alkyl), 2-[4-benzyl-1-piperazinyl]-ethyl- (the phenyl moiety may be substituted in the o, m, or p- position with $NH_2$, OH, $OCH_3$, halogen, alkyl), 2-[4-(o-methylbenzyl)-1-piperazinyl]-ethyl- (the phenyl moiety may be substituted in the o, m, or p- position with $NH_2$, OH, $OCH_3$, halogen, alkyl) or lower alkyl esters thereof (1 to 6 carbons) such as 4-propionoxy-4-phenyl-1-piperidinylethyl; dialkylaminoalkyl; 2-(1-adamantyl)-ethyl- (the adamantyl moiety may be substituted with $NH_2$, OH, $OCH_3$, halogen, alkyl);

$R^1$ is hydrogen, lower alkyl, phenyl or phenyl lower alkyl;

$R^2$ is hydrogen or lower alkyl;

$R^3$ is hydrogen, lower alkoxy e.g. $-OCH_3$, methoxy methyl, lower alkoxy alkyl ether of hydroxy e.g. $-O-CH_2-OCH_3$, amino, lower alkyl, halogen, nitro, hydroxy, or carboxylic acid ester of hydroxy group e.g. $-OCOR^4$ wherein $R^4$ is lower alkyl, pyridine or adamantane.

Being organic bases the above compounds readily form salts with organic or inorganic acids such as hydrochloric, maleic, tartaric, sulfuric, and other nontoxic acids to form pharmaceutically acceptable acid addition salts.

Particularly satisfactory compounds from the point of view of analgesia and narcotic antagonism are compounds in which $R^3$ is hydroxy or lower alkoxy.

The following examples of specific compounds and their preparation are given to illustrate the invention, it being understood that other compounds of the general formula may be made by routine modifications within the skill of the art.

EXAMPLE 1

PREPARATION OF 7-Methoxy-1,2,4,5-tetrahydro-3H,3-benzazepine

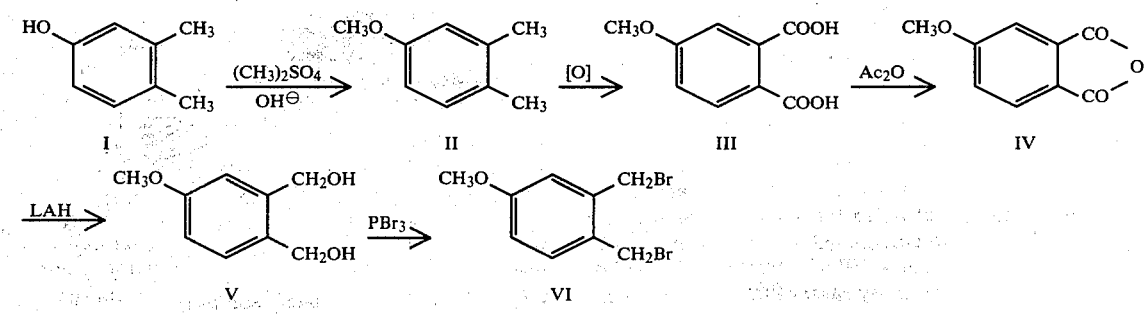

EXAMPLE 1
PREPARATION OF 7-Methoxy-1,2,4,5-tetrahydro-3H,3-benzazepine

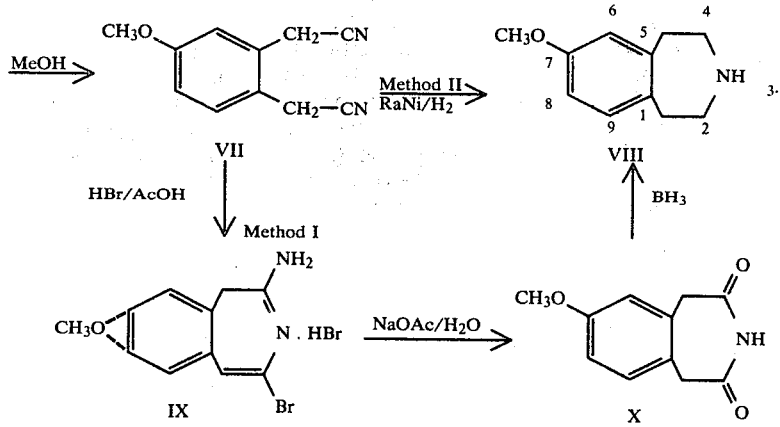

3,4-Dimethyl anisole 3,4-Dimethylphenol (1 kg., 8.2 m) was suspended in water (3,300 ml.) and the stirred mixture was warmed to 45° C. The heat source was removed. With constant stirring, dimethyl sulfate (1,310 gm., 10.4 m) and a solution of sodium hydroxide (576 gm., 14.4) in water (1,480 ml.) were added in alternate portions so that the heat of reaction maintained the temperature at 47°–50° C. The addition took about 5 hours. The resulting mixture was stirred at room temperature for a further 3 hours and then it was allowed to stand overnight at room temperature.

The reaction mixture was extracted with chloroform (1×800 ml., 3×400 ml.). The combined chloroform layers were washed with water (3×200 ml.). After drying the chloroform solution over anhydrous magnesium sulfate, the solvent was evaporated on a rotary evaporator at 15 mm. The light yellow oil which remained was distilled at 7 mm pressure and the fraction boiling at 85°–88° was collected. wt. =942 gm.

4-Methoxyphthalic acid 3,4-Dimethylanisole (250 gm., 1.8 m) was suspended in water (7 l.) at 70° C. Potassium permanganate (2 kg., 12.6 m) was added portionwise at a rate which maintained the temperature between 75°–85° C. The addition was complete in 5 hours. The reaction was stirred a further 3 hours, without heating and then it was allowed to stand overnight at room temperature. The precipitated manganese dioxide was removed by suction filtration. Sodium chloride (1,500 gm.) was added to the filtrate which was then acidified with conc. hydrochloric acid to pH 1-2 (approx. 800 ml.). The precipitated solid was extracted into ethyl acetate (3×1 l.). The ethylacetate extract was dried over anhydrous magnesium sulfate and then the solvent was evaporated at 15 mm. The residual solid had m.p. 168°–174°. wt.=240 gm.

4-Methoxyphthalic anhydride

4-Methoxyphthalic acid (959 gm., 5.06 m) and acetic anhydride (2 l.) were mixed together and warmed to reflux. After 2 hours at reflux the solution was filtered while hot. The filtrate was cooled to room temperature and then it was cooled at −70° C. overnight. The solid precipitate was recovered by suction filtration, washed with petroleum either (40°–60°) and air dried. wt.=649 gm., m.p. 89°–94° C.

The acetic anhydride mother liquors were evaporated to dryness at 15 mm. The residue was dissolved in ethyl acetate(1 l.) and the solution was washed with water (2×500 ml.) saturated sodium carbonate solution (2×500 ml.), water (500 ml.) and saturated saline solution (500 ml.). The ethyl acetate was dried over anhydrous magnesium sulfate and evaporated at 15 mm. The solid obtained had m.p. 89°–93°. wt.=103 gm.

4-Methoxy-o-xylenol

Lithium aluminum hydride(75 gm., 1.98 m) was suspended in tetrahydrofuran (2 l.) in an atmosphere of nitrogen at room temperature. To the stirred suspension was added dropwise a solution of 4-methoxyphthalic anhydride (250 gm., 1.40 m) in tetrahydrofuran (500 ml.) during 3 hours. The resulting reaction mixture was warmed to reflux for 2 hours and then it was allowed to stand at room temperature overnight. Water (75 ml.), 15% sodium hydroxide solution (75 ml.) and water (225 ml.) were added successively to the stirred, ice-cooled reaction mixture. Stirring was continued for a further hour, then the salts were filtered off. The filtrate waas dried over magnesium sulfate. The dried solvent was evaporated at 15 mm. A colorless oil was obtained which solidified on standing to give the diol. m.p. 69°–73° C. wt.=217 gm. b.p. 146° C./0.025 mm.

Anal. Calc. for $C_9H_{12}O_3$: C, 64.27; H, 7.19. Found C. 64.01; H, 7.43.

4-Methoxy-α, α'-dibromo-o-xylene

4-Methoxy-o-xylenol (250 gm., 1.49 m) was suspended in dichloromethane (2.5 l.) at room temperature. Phosphorous tribromide (417 gm., 1.49 m) was added dropwise during 5½ hours. The temperature never exceeded 35° C. The first 100 ml. of bromide was added in 5 hours, and the remainder in 30 minutes. The reaction was stirred for a further 2 hours then it was cooled to 10° and water (500 ml.) was added in 10 minutes. The temperature remained below 25°. After a further 5 minutes the dichloromethane was separated and washed with saturated sodium carbonate solution (500 ml.), water (2×400 ml.) and saturated brine solution (400 ml.). The dichloromethane solution was dried over magnesium sulfate. Evaporation of the solvent at 15 mm pressure afforded a solid m.p. 48°-50°. wt.=430 gm.

The product was recrystallized from petroleum ether (40°-60°). m.p. 49°-49.5°.

Anal. Calc. for $C_9H_{10}Br_2O$: C, 37.04; H, 3.43; Br, 54.36. Found: C, 37.15; H, 3.60; Br, 54.42.

4-Methoxy-o-phenylenediacetonitrile

Finely ground sodium cyanide (73 gm., 1.48 m) was suspended in dimethylsulfoxide (500 ml.) by means of a "Vibro-Mixer". A solution of 4-Methoxy-$\alpha,\alpha'$-dibromo-o-xylene (113 gm., 0.384 m) in dimethylsulfoxide (200 ml.) was added dropwise to the cyanide suspension. The internal temperature was kept at 35°-38° C. by means of an ice bath. The addition took 15 minutes. Agitation of the reaction was continued for a further 1½ hours. The reaction mixture was poured into water (4 l.). The aqueous mixture was extracted with ether (2×1 l., 3×500 ml.) and the combined ether extracts were washed with dilute hydrochloric acid (6 N) (2×500 ml.), saturated sodium carbonate solution (1×500 l ml.), water (3×500 ml.) and saturated sodium chloride solution (2×500 ml.). The ether layer was dried over magnesium sulfate. The dried ethereal solution was evaporated to an oil which was distilled and the fraction with boiling range 160°-165° (0.1 mm) was collected. wt.=53 gm. The oil obtained was crystallized from ether (650 ml.) to give 45 gm. (m.p. 51°-53°). A second drop of 5.8 gm.(m.p. 49°-51°) was obtained.

Anal. Calc. for $C_{11}H_{10}N_2O$: C, 70.78; H, 5.48; N, 14.90.

Found: C, 70.95; H, 5.41; N, 15.05.

4-Methoxy-o-phenylenediacetimide

4-Methoxy-o-phenylenediacetonitrile (135 gm., 0.725 m) was dissolved in acetic acid (180 ml.) and added dropwise during 30 minutes to a solution of hydrobromic acid in acetic acid (32%, 500 gm.) at 15°-20° C. The reaction was stirred at room temperature for 4 hours. The precipitated solid was filtered and washed with acetic acid until the solid was colorless. The solid was washed with acetone and air dried. wt.=196 gm.

The above solid was added to water (3.5 l.) which had been preheated to 85°. When the solid had been dissolved anhydrous sodium acetate (48 gm., 0.59 m) was added during five minutes. The temperature rose to 93° and it was maintained at 92°-93° C. for 1 hour. The heat source was removed and the reaction was stirred for 45 minutes while the temperature dropped to 70°. The warm reaction was filtered to give the required imide. m.p. 180°-183°, wt.=105 gm. The imide was recrystallized from absolute methanol m.p.=181°-183°.

Anal. Calc. for $C_{11}H_{11}NO_3$: C, 64.38; H, 5.40; N, 6.83. Found: C, 64.57; H, 5.59; N, 6.62.

7-Methoxy-1,2,4,5-tetrahydro-3H,3-benzazepine

Method I

4-Methoxy-o-phenylenediacetimide (50 gm., 0.245 m) was added portionwise during 20 minutes to a solution of borane in tetrahydrofuran (1 l., 1 m in BH$_3$) which was being stirred at 10° C. in an atmosphere of nitrogen. The solution was stirred at room temperature for 5 hours. Hydrochloric acid (6 N, 20 ml.) was added to the stirred, ice-cooled reaction during 45 minutes. The initial foaming subsided and a further 230 ml. of hydrochloric acic (6 N) was added during 30 minutes. The suspension was stirred at room temperature for 16 hours and then the insolubles were filtered. The filtrate was evaporated to dryness at 15 mm. and the residual solid was treated with water (500 ml.). The aqueous mixture was filtered and the filtrate was basified with 10% sodium hydroxide solution. The precipitated oil was extracted into benzene (1 l.) and the benzene extract was dried over magnesium sulfate. Evaporation of the benzene afforded an oil (32 gm.) which was distilled at 0.05 mm. The fraction was the boiling range 90°-93° was collected wt.=28.0 gm.

The amine was analyzed as the maleate salt which was recrystallized from methyl ethyl ketone. m.p. 140°-141°.

Anal. Calc. for $C_{11}H_{15}NO \cdot C_4H_4O_4$: C, 61.42; H, 6.53; N, 4.78. Found: C, 61.52; H, 6.74; N, 4.93.

Method II

A Parr hydrogenation bomb (1 l.) was charged with 4-methoxy-o-phenylenediacetonitrile (75 gm. 0.403 m), absolute ethanol (500 ml.) and Raney-Nickel catalyst (Raney #28 in water, 50 gm. of wet catalyst). The catalyst was washed several times with absolute ethanol before it was added. The bomb was heated until the solution temperature was 90° C. and the hydrogen pressure was 1000 psi. Stirring was begun and heating was stopped. The reduction was carried out at 1000-700 psi and the stirring was continued until the temperature had dropped to 30° C. The hydrogen pressure reduction was 1760 psi. The catalyst was removed by filtration and the solvent was evaporated. The residual oil was distilled and the fraction with the boiling range 82°-86° (0.01 mm) was collected. wt.=24 gm.

7-Hydroxy-1,2,4,5-tetrahydro-3H,3-benzazepine

EXAMPLE 2

7-Methoxy-1,2,4,5-tetrahydro-3H,3-benzazepine (15 gm., 0.085 m) was refluxed with 48% aqueous hydrobromic acid (120 ml.) for 3 hours. The excess acid was evaporated in vacuo and the residual solid was washed with acetone and filtered to give the salt of the title compound. wt.=19.5 gm. The salt was recrystallized from absolute ethanol. m.p. 248°-249°.

Anal. Calc. for $C_{10}H_{13}NO \cdot HBr$: C, 49.19; H, 5.78; Br, 32.73; N, 5.74. Found: C, 49.15; H, 6.00; Br, 32.44; N, 5.61.

The free amine was obtained by treating the above salt in aqueous solution with an equivalent amount of sodium hydroxide. The solid precipitate was filtered and recrystalized from isopropanol. m.p. 191°-193°.

Anal. Calc. for $C_{10}H_{13}NO$: C, 73.59; H, 8.03; N, 8.58. Found: C, 73.34; H, 8.03; N, 8.71.

ROUTES TO 3-SUBSTITUTED BENZAZEPINES

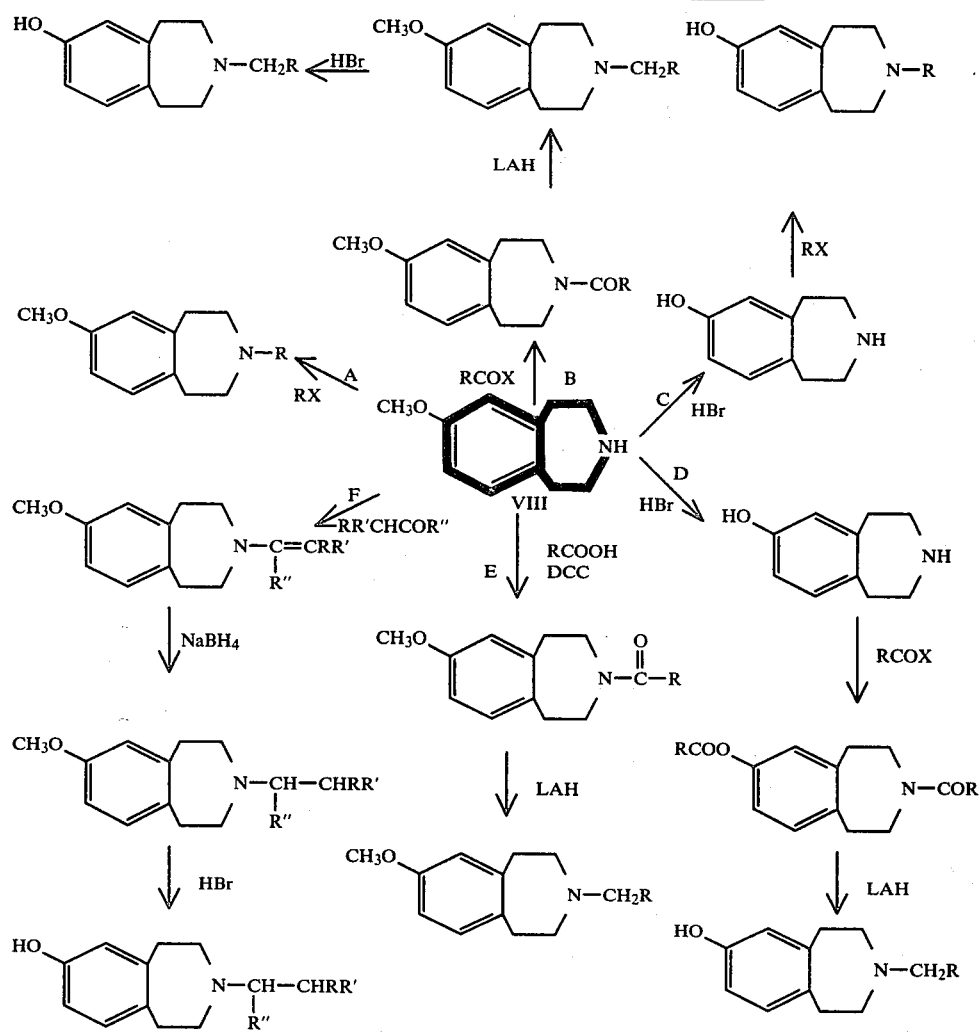

EXAMPLE 3

3-(3,3-Dimethylallyl)-7-methoxy-1,2,4,5-tetrahydro-3H,3-benzazepine (Method A)

7-Methoxy-1,2,4,5-tetrahydro-3H,3-benzazepine (17.7 gm., 0.1 m), triethylamine (10.1 gm. 0.1 m) benzene (200 ml.) and dimethylformamide (40 ml.) were mixed and stirred at room temperature. 1-Chloro-3-methyl-2-butene (10.7 gm., 0.107 m) was added dropwise during 15 minutes. The reaction was stirred for 4 hours and then water (200 ml.) was added. The benzene layer was separated and washed with water. After drying over magnesium sulfate the benzene was evaporated in vacuo to give an oil. wt.=20.5 gm. The oil was purified by chromatography on silica gel and elution with benzene:methanol (9:1). The pure amine (15.7 gm.) was converted to the hydrochloride salt and recrystallized from isopropanol. m.p. 204°–206.5°.

Anal. Calc. for $C_{16}H_{23}NO \cdot HCl$: C, 68.21, H, 8.58; N, 4.97; Cl, 12.58. Found: C, 68.14; H, 8.69; N, 5.00; Cl, 12.71.

EXAMPLE 4

3-(3,3-Dimethylallyl)-7-hydroxy-1,2,4,5-tetrahydro-3H,3-benzazepine (Method C)

Triethylamine (23.2 gm., 0.23 m) was added to a solution of 7-hydroxy-1,2,4,5-tetrahydro-3H,3-benzazepine hydrobromide (28 gm., 0.115 m) in dimethylformamide (120 ml.) which was being stirred at room temperature. After 5 minutes 1-chloro-3-methyl-2-butene (13.2 gm., 0.127 m) was added dropwise during 15 minutes. The reaction was warmed to 50° C. for 2 hours. Water (200 ml.) was added and the product was isolated by extraction into diethyl ether. The ether extract was dried over magnesium sulfate and then the ether was evaporated to give a solid. The solid was triturated with cyclohexane and filtered to give the title compound. wt.=20 gm. The amine was converted to the hydrochloride salt and recrystallized from absolute methanol. m.p. 254.5°–256° C.

Anal. Calc. for $C_{15}H_{21}NO \cdot HCl$: C, 67.30; H, 8.38; N, 5.23; Cl, 13.24. Found: C, 67.48; H, 8.34; N, 5.32; Cl, 13.39.

EXAMPLE 5

7-Acetoxy-3-(3,3-dimethylallyl)-1,2,4,5-tetrahydro-3H,3-benzazepine hydrochloride (807-682)

3-(3,3-Dimethylallyl)-7-hydroxy-1,2,4,5-3H,3-benzazepine hydrochloride (5 g) was suspended in 50 ml tetrahydrofuran and 8.63 ml triethylamine. A solution of 2.98 ml acetyl chloride in 10 ml tetrahydrofuran was added over 30 minutes at reflux. The mixture was filtered, the filtrate concentrated to dryness and the residue dissolved in ether. The ether solution was treated with HCl gas and the solid filtered and recrystallized from isopropanol to give 4 g of the product.

|    | Calcd | Found |
|----|-------|-------|
| C  | 65.90 | 65.77 |
| H  | 7.81  | 7.92  |
| Cl | 11.44 | 11.51 |
| N  | 4.52  | 4.42  |

EXAMPLE 6

7-(Adamantanecarbonyloxy)-3-(3,3-dimethylallyl)-1,2,4,5-tetrahydro-3H,3-benzazepine hydrochloride (766-458)

A solution of 0.03 moles of adamantanecarbonyl chloride in 15 ml benzene was added dropwise during ½ hr to 3-(3,3-dimethylallyl)-7-hydroxy-1,2,4,5-tetrahydro-3H,3-benzazepine hydrochloride (7.5 g) in 40 ml dimethylformamide containing 6.05 g triethylamine at 10°–15° C. After 4 hrs at room temperature, the mixture was warmed to 70°, kept there for 2 hrs, and finally heated 16 hrs at 85°. The mixture was diluted with water and extracted with chloroform. The chloroform extract was washed with water, dried, and concentrated to dryness. The residue was triturated with isopropyl ether to give 3 g of a gummy solid which was chromatographed on silica. The main fraction gave an oily material which was treated with isopropyl ether to give a small amount of solid. The isopropyl ether filtrate was treated with HCl gas and the resultant solid recrystallized twice from isopropanol and dried 16 hrs at 80° to give the product, m 240°–245°.

|    | Calcd | Found |
|----|-------|-------|
| C  | 72.61 | 72.85 |
| H  | 8.44  | 8.75  |
| Cl | 8.24  | 8.35  |
| N  | 3.26  | 3.23  |

EXAMPLE 7

3-Cyclopropylmethyl-7-methoxy-1,2,4,5-tetrahydro-3H,3-benzazepine (method B)

A solution of cyclopropanecarboxylic acid chloride (10 gm., 0.0955 m) in tetrahydrofuran (50 ml.) was added dropwise to a solution of 7-methoxy-1,2,4,5-tetrahydro-3H,3-benzazepine (13 gm., 0.0735 m) and pyridine (6.9 gm., 0.087 m) in tetrahydrofuran (100 ml.) at 0° during 30 minutes. The reaction was stirred at room temperature for a further 2 hours. Water (200 ml.) was added and the tetrahydrofuran was evaporated in vacuo. The amide was extracted into diethyl ether and the ether layer was washed with 5% sodium hydroxide solution and hydrochloric acid (3N). After drying the ether extract over magnesium sulfate the solvent was evaporated in vacuo to give the amide.

The amide can be recrystallized from cyclohexane to give pure 3-cyclopropylcarbonyl-7-methoxy-1,2,4,5-tetrahydro-3H,3-benzazepine. m.p. 58(°–60°.

Anal. Calc. for $C_{15}H_{19}NO_2$: C. 73.44; H, 7.81; N, 5.71. Found: C, 73.69; H, 7.79; N, 5.99.

The crude amide was dissolved in tetrahydrofuran (100 ml.) and added dropwise to a suspension of lithium aluminum hydride (2.5 gm., 0.066 m) in refluxing tetrahydrofuran (250 ml.) during 30 minutes. The reaction was refluxed for a further 2 hours. The cooled reaction was decomposed by the successive addition of water (2.5 ml.), 15% sodium hydroxide solution (2.5 ml.) and water (7.5 ml.). The tetrahydrofuran solution was filtered and dried over magnesium sulfate. Evaporation of the solvent in vacuo afforded the amine as an oil. wt. = 13 gm. The amine was converted to the hydrochloride salt which was recrystallized from isopropanol. m.p. 222°–223°.

Anal. Calc. for $C_{15}H_{21}NO \cdot HCl$: C, 67.28; H, 8.28; N, 5.23; Cl, 13.24. Found: C, 66.98; H, 8.16; N, 5.08; Cl, 13.00.

EXAMPLE 8

3-Cyclopropylmethyl-7-hydroxy-1,2,4,5-tetrahydro-3H,3-benzazepine (Method D)

Triethylamine (17.7 gm., 0.175 m) was added to a solution of 7-hydroxy-1,2,4,5-tetrahydro-3H,3-benzazepine hydrobromide (13 gm., 0.053 m) in dimethylformamide (50 ml.) which was being stirred at room temperature. After 5 minutes, the reaction was cooled to 0° C. and cyclopropanecarboxylic acid chloride (13 gm., 0.124 m) was added dropwise during 10 minutes. The reaction was stirred at room temperature for 1 hour. Water (100 ml.) was added to the reaction and the precipitate was extracted into ethyl acetate (300 ml.). The ethyl acetate extract was washed with 10% sodium hydroxide solution and hydrochloric acid (3N). The ethyl acetate layer was dried over magnesium sulfate and evaporated in vacuo to give the crude amide. wt. = 14 gm. The amide was recrystallized from diisopropyl ether. m.p. 87°–89°.

Anal. Calc. for $C_{18}H_{21}NO_3$: C, 72.21; H, 7.07; N, 4.68. Found: C, 72.48; H, 6.99; N, 4.62.

A solution of 3-cyclopropylcarbonyl-7-cyclopropylcarbonyloxy-1,2,4,5-tetrahydro-3H,3-benzazepine (18 gm. 0.06 m) in tetrahydrofuran (200 ml.) was added dropwise to a suspension of lithium aluminum hydride (5 gm., 0.132 m) in tetrahydrofuran (500 ml.) at room temperature during 30 minutes. The reaction was stirred at room temperature for 18 hours. Ethyl acetate (50 ml.) was added cautiously, followed by a saturated aqueous solution (750 ml.) of ammonium tartrate. The reaction was stirred for a further 1 hour. Two layers formed and the tetrahydrofuran layer was separated. The solvent was evaporated in vacuo and the residue was dissolved in chloroform. The chloroform solution was washed with water and dried over magnesium sulfate. Evaporation of the chloroform in vacuo afforded the title compound as a solid. wt. = 12 gm. The amine was converted to the hydrochloride salt which was recrystallized from isopropanol m.p. 220°–222°.

Anal. Calc. for $C_{14}H_{19}NO \cdot HCl$: C, 66.24; H, 7.94; N, 5.52; Cl, 13.97. Found: C, 66.13; H, 7.74; N, 5.30; Cl, 13.89.

EXAMPLE 9

3-Cyclobutylmethyl-7-hydroxy-1,2,4,5-tetrahydro-3H,3-benzazepine (Method D)

Triethylamine (27.8 gm., 0.275 m) was added to a solution of 7-hydroxy-1,2,4,5-tetrahydro-3H,3-benzazepine hydrobromide (19.5 gm., 0.08 m) in dimethylformamide (90 ml.) which was being stirred at room temperature. After 5 minutes the reaction was cooled to 0° C. and cyclobutanecarboxylic acid chloride (22 gm., 0.186 m) was added dropwise during 15 minutes. The reaction was stirred at room temperature for 3 hours. Water (200 ml.) was added to the reaction and the precipitate was extracted into ethyl acetate (400 ml.). The ethyl acetate extract was washed with hydrochloric acid (3N) and sodium bicarbonate solution. The ethyl acetate layer was dried over magnesium sulfate and evaporated in vacuo to give the crude amide. wt.=26 gm. The amide was recrystallized from diisopropyl ether. m.p. 96°–98°.

Anal. Calc. for $C_{25}H_{25}NO_3$: C, 73.36; H, 7.70; N, 4.28. Found: C, 73.60; H, 7.64; N, 4.50.

A solution of 3-cyclobutylcarbonyl-7-cyclobutylcarbonyloxy-1,2,4,5-tetrahydro-3H,3-benzazepine (18 gm., 0.055 m) in tetrahydrofuran (200 ml.) was added dropwise to a suspension of lithium aluminum hydride (5 gm., 0.132 m) in tetrahydrofuran (500 ml.) at room temperature during 30 minutes. The reaction was stirred at room temperature for 20 hours. Ethyl acetate (50 ml) was added cautiously followed by a saturated aqueous solution (500 ml.) of ammonium tartrate. The reaction was stirred for a further 1 hour. Two layers formed and the tetrahydrofuran layer was separated. The solvent was evaporated in vacuo and the residue was dissolved in chloroform. The chloroform solution was washed with water and dried over magnesium sulfate. Evaporation of the chloroform in vacuo afforded a semi-solid which was triturated with diethyl ether and filtered to give the title compound. wt.=9.3 gms.

The amine was converted to the hydrochloride salt which was recrystallized from methanol:diethyl ether. m.p. 252°–254°.

Anal. Calc. for $C_{15}H_{21}NO$ . HCl: C, 67.30; H, 8.28; N, 5.23; Cl, 13.24. Found: C, 67.03; H, 8.06; H, 5.49; Cl, 13.00.

EXAMPLE 10

3-Cyclopentylmethyl-7-hydroxy-1,2,4,5-tetrahydro-3H,3-benzazepine (Method D)

Triethylamine (19.4 gm., 0.191 m) was added to a solution of 7-hydroxy-1,2,4,5-tetrahydro-3H,3-benzazepine hydrobromide (12 gm., 0.049 m) in dimethylformamide (60 ml.) which was being stirred at room temperature. After 5 minutes, the reaction was cooled to 0° C. and cyclopentanecarboxlic acid chloride (15.6 gm., 0.117 m) was added dropwise during 5 minutes. The reaction was stirred at room temperature for 3 hours. Water (200 ml.) was added and the precipitate was extracted into ethyl acetate (300 ml.). The ethyl acetate extract was washed with hydrochloric acid (3N) and sodium carbonate solution. The ethyl acetate layer was dried over magnesium sulfate and evaporated in vacuo to give the crude amide-ester as an oil. wt.=17.5 gm.

The above oil (17.5 g., 0.049 m) was dissolved in tetrahydrofuran (150 ml.) and the solution was added dropwise to a suspension of lithium aluminum hydride (3 gm., 0.079 m) in tetrahydrofuran (400 ml.) at room temperature during 30 minutes. The reaction was stirred at room temperature for 17 hours. The complex was decomposed by the successive addition of water (3 ml.), 15% sodium hydroxide solution (3 ml.) and water (9 ml.). The resultant emulsion was treated with carbon dioxide until pH=8.5 had been attained. The tetrahydrofuran solution was filtered from the salts, dried over magnesium sulfate and evaporated in vacuo. The resultant oil was dissolved in refluxing diisopropyl ether (100 ml.) and on cooling the title compound precipitated as a crystalline solid. wt.=8 gm. The amine was converted to the hydrochloride salt which was recrystallized from absolute ethanol. m.p. 263°–265°.

Anal. Calc. for: $C_{16}H_{23}NO$ . HCl: C, 68.21; H, 8.58; N, 4.97; Cl, 12.58. Found: C, 68.02; H, 8.49; N, 4.92; Cl, 12.58.

EXAMPLE

3-Allyl-7-hydroxy-1,2,4,5tetrahydro-3H,3-benzazepine (Method C)

Triethylamine (8.25 gm., 0.082 m)was added to a solution of 7-hydroxy-1,2,4,5-tetrahydro-3H,3-benzazepine hydrobromide (10 gm., 0.041 m) in dimethylformamide (35 ml.) which was being stirred at room temperature. After 5 minutes, allylbromide (4.96 gm., 0.041 m) was added dropwise during 15 minutes. The reaction was stirred at room temperature for 3 hours. Water (100 ml.) was added and the product was isolated by extraction into ethyl acetate. The ethyl acetate layer was dried over magnesium sulfate and evaporated in vacuo to give the title compound as a solid. wt.=6.4 gm. The amine was converted to the hydrochloride salt which was recrystallized from isopropanol. m.p. 176°–178°.

Anal, Calc. for $C_{13}H_{17}NO \cdot HCl$: C, 65.13; H, 7.57; N, 5.84; Cl, 14.79. Found: C, 64.82; H, 7.37; N, 5.59; Cl, 14.71.

EXAMPLE 12

3-Cyclopentylmethyl-7-methoxy-1,2,4,5-tetrahydro-3H,3-benzazepine (Method B)

A solution of cyclopentanecarboxylic acid chloride (9 gm., 0.068 m) in benzene (20 ml.) was added dropwise to a solution of 7-methoxy-1,2,4,5-tetrahydro-3H,3-benzazepine (10 gm., 0.056 m) and triethylamine (5.65 gm., 0.056 m) in benzene (100 ml.) at 0° during 10 minutes. The reaction was stirred at room temperature for 2 hours. Water (50 ml.) was added and the benzene extract was separated. The benzene extract was washed with hydrochloric acid (3N) and sodium carbonate solution and then it was dried over magnesium sulfate. Evaporation of the benzene in vacuo afforded the amide as an oil. wt.=15 gm.

The crude amide was dissolved in tetrahydrofuran (60 ml.) and added dropwise to a suspension of lithium aluminum hydride (2.12 gm., 0.056 m) in tetrahydrofuran (90 ml.) during 30 minutes at room temperature. The reaction was stirred at room temperature for 2.5 hours. The complex was decomposed by the successive addition of water (2.1 ml), 15% sodium hydroxide solution (2.1 ml.) and water (6.3 ml.). The tetrahydrofuran solution was filtered and dried over magnesium sulfate. Evaporation of the solvent in vacuo afforded the amine as an oil which was converted to the hydrochloride salt. wt.=14.4 gm. The salt was recrystallized from isopropanol. m.p. 250°–252°.

Anal. Calc. for $C_{17}H_{25}NO \cdot HCl$: C, 69.03; H, 8.86; N, 4.74; Cl, 11.99. Found: C, 68.87; H, 8.71; N, 4.98; Cl, 11.90.

EXAMPLE 13

3-Cyclobutylmethyl-7-methoxy-1,2,4,5-tetrahydro-3H,3-benzazepine (Method B)

A solution of cyclobutanecarboxylic acid chloride (8.05 gm., 0.068 m) in benzene (20 ml.) was added dropwise to a solution of 7-methoxy-1,2,4,5-tetrahydro-3H,3-benzazepine (10 gm., 0.056 m) and triethylamine (5.65 gm., 0.056 m) in benzene (100 ml.) at 0° during 10 minutes. The reaction was stirred at room temperature for 2 hours. Water (50 ml.) was added and the benzene extract was separated. The benzene extract was washed with hydrochloric acid (3N) and sodium carbonate solution and then it was dried over magnesium sulfate. Evaporation of the benzene in vacuo afforded the amide as an oil.

The crude amide was dissolved in tetrahydrofuran (60 ml.) and added dropwise to a suspension of lithium aluminum hydride (2.12 gm., 0.056 m) in tetrahydrofuran (50 ml.) during 30 minutes at room temperature. The reaction was stirred at room temperature for 2.5 hours. The complex was decomposed by the successive addition of water (2.1 ml.), 15% sodium hydroxide solution (2.1 ml.) and water (6.3 ml.). The tetrahydrofuran solution was filtered and dried over magnesium sulfate. Evaporation of the solvent in vacuo afforded the amine as an oil which was converted to the hydrochloride salt. wt.=14.2 gm. The salt was recrystallized from isopropanol:methanol (10:1). m.p. 235°–236°.

Anal. Calc. for $C_{16}H_{23}NO \cdot HCl$: C, 68.21; H, 8.58; N, 4.97; Cl, 12.58. Found: C, 67.95; H, 8.64; N, 5.09; Cl, 12.64.

EXAMPLE 14

3-Allyl-7-methoxy-1,2,4,5-tetrahydro-3H,3-benzazepine (Method A)

7-Methoxy-1,2,4,5-tetrahydro-3H,3-benzazepine (5 gm., 0.0282 m), triethylamine (2.85 gm., 0.0282 m), benzene (30 ml.) and dimethylformamide were mixed and stirred at room temperature. A solution of 3-bromopropane (3.42 gm., 0.0282 m) in benzene (20 ml.) was added dropwise during 10 minutes. The reaction was stirred at room temperature for 3 hours and then water (60 ml.) was added. The benzene layer was separated and washed with water. After drying over magnesium sulfate the benzene was evaporated in vacuo to give the title compound as an oil. The amine was cnverted to the hydrochloride salt. wt.=6.2 gm. The salt was recrystallized from methylethylketone:methanol (10:1). m.p. 196°–199°.

Anal. Calc. for $C_{14}H_{19}NO \cdot HCl$: C, 66.24; H, 7.94; N, 5.52; Cl, 13.97. Found: C, 66.49; H, 8.11; N, 5.67; Cl, 14.15.

EXAMPLE 15

7-Hydroxy-3-(2-methylallyl)-1,2,4,5-tetrahydro-3H,3-benzazepine (Method C)

Triethylamine (8.25 gm. 0.082 m) was added to a solution of 7-hydroxy-1,2,4,5-tetrahydro-3H,3-benzazepine hydrobromide (10 gm., 0.041 m) in dimethyl-formamide (50 ml.) which was being stirred at room temperature. After 5 minutes methallyl chloride (3.72 gm., 0.041 m) was added dropwise during 15 minutes. The reaction was warmed to 50° and stirred for 3 hours. Water (100 ml.) was added and the product was isolated by extraction into ethyl acetate. The ethyl acetate layer was dried over magnesium sulfate and evaporated in vacuo to give the title compound as a solid which was converted to the hydrochloride salt. wt.=8.5 gm. The salt was recrystallized from isopropanol: methanol (4:1). m.p. 219°–221°.

Anal Calc. for $C_{14}H_{19}NO \cdot HCl$: C, 66.24; H, 7.94; N, 5.52; Cl, 13.97. Found: C, 66.01; H, 7.72; N, 5.49; Cl, 13.82.

EXAMPLE 16

7-Methoxy-3-propargyl-1,2,4,5-tetrahydro-3H,3-benzazepine (Method A)

7-Methoxy-1,2,4,5-tetrahydro-3H,3-benzazepine (5 gm., 0.0282 m), triethylamine (2.85 gm., 0.0282 m), dimethylformamide (10 ml.) and benzene (40 ml.) were mixed and stirred at room temperature. A solution of 3-bromopropyne (3.45 gm., 0.029 m) in benzene (20 ml.) was added dropwise during 5 minutes. The reaction was stirred at room temperature for 3 hours and then water (60 ml.) was added. The benzene layer was separated and washed with water. After drying over magnesium sulfate the benzene was evaporated in vacuo to give the title compound as an oil. The amine was converted to the hydrochloride salt. wt.=6.3 gm. The salt was recrystallized from methylethylketone:methanol (10:1). m.p. 194°–195°.

Anal. Calc. for $C_{14}H_{17}NO \cdot HCl$: C, 66.77; H, 7.20; N, 5.56; Cl, 14.08. Found: C, 66.68; H, 7.29; N, 5.43; Cl, 14.09.

EXAMPLE 17

7-Hydroxy-3-propargyl-1,2,4,5-tetrahydro-3H,3-benzazepine (Method C)

Triethylamine (8.7 gm., 0.0864 m) was added to a solution of 7-hydroxy-1,2,4,5-tetrahydro-3H,3-benzazepine hydrobromide (10.54 gm., 0.0432 m) in dimethylformamide (50 ml.) which was being stirred at room temperature. After 5 minutes, 3-bromopropyne (5.16 gm., 0.0432 m) was added dropwise during 5 minutes. The reaction was stirred at room temperature for 4 hours. Water (100 ml.) was added and the product was isolated by extraction into ethyl acetate. The ethyl acetate layer was dried over magnesium sulfate and evaporated in vacuo to give the title compound as a solid which was converted to the hydrochloride salt. wt.=11.3 gm. The salt was recrystallized from isopropanol:methanol (1:1), m.p. 201°–202°.

Anal. Calc. for $C_{13}H_{15}NO \cdot HCl$: C, 65.69; H, 6.79; N, 5.89; Cl, 14.92. Found: C, 65.89; H, 6.98; N, 6.Cl; Cl, 15.16.

EXAMPLE 18

7-Methoxy-3-methyl-1,2,4,5-tetrahydro-3H,3-benzazepine 7-methoxy-1,2,4,5-tetrahydro-3H,3-benzazepine (10 gm., 0.0565 m) was dissolved in a solution of formalin (24 ml.) and formic acid (28 ml.) and refluxed for 6 hours. After standing at room temperature for 16 hours, the solvents were evaporated in vacuo and the residue was shaken with 10% sodium hydroxide solution and diethyl ether. The ether extract was washed with water and dried over magnesium sulfate. Evaporation of the ether in vacuo afforded the title compound as an oil which was converted to the hydrochloride salt.

wt.=10.0 gm. The salt was recrystallized from methylethylketone:methanol. m.p. 188°-190°.

Anal. Calc. for $C_{12}H_{17}NO \cdot HCl$: C, 63.29; H, 7.97; N, 8.15; Cl, 15.57. Found: C, 63.16; H, 7.74; N, 6.08; Cl, 15.80.

EXAMPLE 19

7-Hydroxy-3-methyl-1,2,4,5-tetrahydro-3H,3-benzazepine

7-Methoxy-3-methyl-1,2,4,5-tetrahydro-3H,3-benzazepine (16 gm., 0.0837 m) was dissolved in 48% aqueous hydrobromic acid (120 ml.) and refluxed for 3 hours. The excess acid and water were evaporated in vacuo. The solid residue was dissolved in water and basified with saturated sodium carbonate solution. The precipitated product was extracted into ethyl acetate. The ethyl acetate layer was dried over magnesium sulfate and evaporated in vacuo to give the title compound as a solid which was recrystallized from diisopropyl ether:methanol. m.p. 142°-146°, wt.=11 gm. The amine was converted to the hydrochloride salt. wt.=10.8 gm. The salt was recrystallized from methanol. m.p. 244°-248°.

Anal. Calc. for $C_{11}H_{15}NO \cdot C$, 61.81; H, 7.55; N, 6.56; Cl, 16.59. Found C, 61.81; N, 7.62; N, 6.47; Cl, 16.72.

EXAMPLE 20

3-Ethyl-7-methoxy-1,2,4,5-tetrahydro-3H,3-benzapine (Method B)

A solution of acetyl chloride (13.4 gm., 0.170 m) in benzene (50 ml.) was added dropwise to a solution of 7-methoxy-1,2,4,5-tetrahydro-3H,3benzazepine (23.8 gm., 0.134 m) and pyridine (13.7 gm., 0.174 m) in benzene (200 ml.) at room temperature during 15 minutes. The reaction was stirred at room temperature for 2 hours. Water (100 ml.) was added and the benzene extract was separated and dried over magnesium sulfate. Evaporation of the benzene in vacuo afforded a solid which crystallized from diisopropyl ether (150 ml.) m.p. 90°-91°. wt.=26 gm.

Anal. Calc. for $C_{13}H_{17}NO_2$: C,71.20; H, 7.82; N, 6.39 Found: C,71.25; H, 7.87; N, 6.26

A solution of 3-acetyl-7-methoxy-1,2,4,5-tetrahydro-3H,3-benzazepine (16.0 gm., 0.073 m) in tetrahydrofuran (50 ml.) was added dropwise to a suspension of lithium aluminum hydride (3.0 gm., 0.079 m) in tetrahydrofuran (200 ml.) during 30 minutes at room temperature. The reaction was then refluxed for 2 hours. The complex was decomposed by the successive addition of water (3 ml.), 1% sodium hydroxide solution (3 ml.) and water (9 ml.) The tetrahydrofuran solution was filtered and dried over magnesium sulfate. Evaporation of the solvent in vacuo afforded the amine as an oil which was converted to the hydrochloride salt and recrystallized from methanol; diethyl ether (1:1). m.p. 219°-221°. wt.=12.5 gm.

Anal. Calc. for $C_{13}H_{19}NO \cdot HCl$: C, 64.58; H, 8.34; N, 5.79; Cl, 14.66 Found: C, 64.55; H, 8.52; N, 5.91; Cl, 14.63.

EXAMPLE 21

3-Ethyl-7-hydroxy-1,2,4,5-tetrahydro-3H,3-benzazepine (Method B)

3-Ethyl-7-Methoxy-1,2,4,5-tetrahydro-3H,3-benzazepine (15 gm), 0.073 m) was dissolved in 48% aqueous hydrobromic acid (250 ml.) and refluxed for 3 hours. The excess acid and water were evaporated in vacuo. The solid residue was dissolved in water and basified with saturated sodium carbonate solution. The precipitated product was extracted into chloroform. The chloroform layer was dried over magnesium sulfate and evaporated in vacuo to give the title compound as a solid which was recrystallized from 50% aqueous ethanol. m.p. 168°-171°. wt.=11.3 gm. The amine was converted to the hydrochloride salt and recrystallized from methanol:diethylether (1:1). m.p. 247°-250°, wt.=11.2 gm.

Anal. Calc. for $C_{12}H_{17}NO \cdot HCl$: C, 63.29; H, 7.97; N, 6.15; Cl, 15.57. Found: C, 63.51; H, 7.87; N, 6.01; Cl, 15.80.

EXAMPLE 22

7-Methoxy-3-n-propyl-1,2,4,5-tetrahydro-3H,3-benzazepine (Method B)

A solution of propionyl chloride (6.5 gm., 0.07 m) in tetrahydrofuran (20 ml.) was added dropwise to a solution of 7-methoxy-1,2,4,5-tetrahydro-'H,3-benzazepine (12 gm., 0.0676 m) and triethylamine (7.04 gm., 0.07 m) in tetrahydrofuran (100 ml.) at 0° during 15 minutes. The reaction was stirred at room temperature for 4 hours. Water (100 ml.) was added and the tetrahydrofuran was evaporated in vacuo. The aqueous residue was extracted with ethyl acetate. The ethyl acetate extract was washed with hydrochloric acid (3N) and 10% sodium hydroxide solution. After drying the ethyl acetate layer over magnesium sulfate the solvent was evaporated in vacuo to give the amide as an oil.

The crude amide was dissolved in tetrahydrofuran (50 ml.) and added dropwise to a suspension of lithium aluminum hydride (2.56 gm., 0.0676 m) in tetrahydrofuran at room temperature during 30 minutes. The reaction was stirred at room temperature for 3 hours. The complex was decomposed by the successive addition of water (2.56 ml.), 15% sodium hydroxide solution (2.56 ml.) and water (7.68 ml.). The tetrahydrofuran solution was filtered and dried over magnesium sulfate. Evaporation of the solvent in vacuo afforded the title compound as an oil. wt.=14 gm. The amine was converted to the hydrochloride salt and recrystallized from methylethylketone, m.p. 208°-210°.

Anal. Calc. for $C_{14}H_{21}NO \cdot HCl$: C, 65.73; H, 8.67;N, 5.48; Cl, 13.86. Found: C, 65.69; H, 8.67; N, 5.54; Cl, 13.92.

EXAMPLE 23

7-hydroxy-3-n-propyl-1,2,4,5-tetrahydro-3H,3-benzazepine (Method B)

7-methoxy-3n-propyl-1,2,4,5,-tetrahydro-3H,3-benzazepine (13 gm., 0.059 m) was dissolved in 48% aqueous hydrobromic acid (100 ml.) and refluxed for 3 hours. The excess acid and water were evaporated in vacuo. The solid residue was dissolved in water and basified with saturated sodium carbonate solution. The precipitated product was extracted into ethyl acetate. The ethyl acetate extract was dried over magnesium sulfate and evaporated in vacuo to give a solid which was triturated with diisopropyl ether and filtered. m.p. 146°-148°. wt=9 gm. The amine was converted to the hydrochloride salt and recrystallized from isopropanol. m.p. 208°-212°.

Anal. Calc. for $C_{13}H_{19}NO \cdot HCl$: C, 64.58; H, 8.34; N, 5.79; Cl, 14.66. Found: C, 64.68; H, 8.38; N, 5.53; Cl, 14.60.

EXAMPLE 24

7-Methoxy-3-phenethyl-1,2,4,5-tetrahydro-3H,3-benzazepine (Method B)

A solution of phenylacetyl chloride (15.5 gm., 0.10 m) chloroform (25 ml.) was added dropwise to a solution of 7-methoxy-1,2,4,5-tetrahydro-3H,3-benzazepine (14.6 gm., 0.08 m) and pyridine (9.25 gm., 0.12 m) in chloroform (100 ml.) at 0° C. during 45 minutes. The reaction was stirred at room temperature for 5 hours. Water (300 ml.) was added and the chloroform extract was separated and dried over magnesium sulfate. Evaporation of the chloroform in vacuo afforded a solid which was triturated with isopropanol and filtered to give the crude amide. m.p. 85.5°–86.5°. wt.=11.4 gm. The amide was recrystallized from isopropanol:diisopropyl ether (3:1). m.p. 86.5°–87.5°.

Anal. Calc. for $C_{19}H_{21}NO_2$: C, 77.26; H, 7.17; N, 4.74. Found: C, 77.25; H, 6.93; N, 4.90.

A solution of 7-methoxy-3-phenylacetyl-1,2,4,5-tetrahydro-3H,3-benzazepine (10.25 gm., 0.034 m) in tetrahydrofuran (45 ml.) was added dropwise to a suspension of lithium aluminum hydride (3.0 gm., 0.079 m) in diethyl ether (75 ml.) during 1 hour at room temperature. The reaction was refluxed for 2 hours. The complex was decomposed by the successive addition of water (3 ml.), 15% sodium hydroxide solution (3 ml.) and water (9 ml.). The solution was filtered from the salts and dried over magnesium sulfate. Evaporation of the solvents in vacuo afforded the amine as an oil. wt.=9.8 gm. The amine was converted to the hydrochloride salt and recrystallized from isopropanol. m.p. 206.5°–207.5°.

Anal. Calc. for $C_{19}H_{23}NO \cdot HCl$: C, 71.76; H, 7.92; N, 4.59; Cl, 11.18. Found: C, 71.80; H, 7.61; N, 4.41; Cl, 11.15.

EXAMPLE 25

7-Hydroxy-3-phenethyl-1,2,4,5-tetrahydro-3H,3-benzazepine (Method B)

7-methoxy-3-phenethyl-1,2,4,5-tetrahydro-3H,3-benzazepine (9.8 gm., 0.034 m) was dissolved in 48% aqueous hydrobromic acid (100 ml.) and refluxed for 2 hours. The excess acid and water were evaporated in vacuo. The solid residue was dissolved in water and basified with saturated sodium carbonate solution. The precipitated solid was filtered and dried. wt.=9 gm. The amine was converted to the hydrochloride salt and recrystallized from water. m.p. 100°–102°. wt.=7 gm.

Anal. Calc. for $C_{18}H_{21}NO \cdot HCl$: C, 71.15; H, 7.30; N, 4.61; Cl, 11.67. Found: C, 71.10; H, 7.23; N, 4.90, Cl, 11.58.

EXAMPLE 26

7-Methoxy-3-(1-methyl-2-phenylethyl)-1,2,4,5-tetrahydro-3H,3-benzazepine (Method F)

7-Methoxy-1,2,4,5-tetrahydro-3H,3-benzazepine (13 gm., 0.0735 m), 1-phenyl-2-propanone (11 gm., 0.082 m) and p-toluenesulfonic acid (0.3 gm.) were dissolved in toluene (100 ml.) and refluxed for 64 hours. The toluene was condensed above a Soxhlet extractor, containing molecular sieves (type 4A), which was attached to a Dean and Stark apparatus. The toluene solution was diluted with absolute methanol (200 ml.) and cooled to 10° C. Sodium borohydride (10 gm., 0.26 m) was added portionwise to the stirred reaction during 15 minutes. The reaction was stirred at room temperature for 4 hours. Water (500 ml.) was added cautiously. The toluene layer was separated and the aqueous solution was further extracted with diethyl ether (300 ml.). The combined ether and toluene extracts were washed with water and then dried over magnesium sulfate. Evaporation of the solvents in vacuo afforded an oil. wt.=22 gm. The oil was purified by chromatograhy on silica gel. Elution of the column with methanol:benzene (1:9), afforded the title compound as an oil which was converted to the hydrochloride salt and crystallized from acetone:diethyl ether (1:1). m.p. 172°–182°, wt.=12.5 gm. The salt was recrystllized from acetone, m.p. 179°–182°. wt=7 gm.

Anal. Calc. for $C_{20}H_{25}NO \cdot HCl$: C, 72.38; H, 7.90; N, 4.22, Cl, 10.68. Found: C, 72.61; H, 7.86; N, 4.30; Cl, 10.61.

EXAMPLE 27

7-Hydroxy-3-(1-methyl-2-phenylethyl)-1,2,4,5-tetrahydro-3H,3-benzazepine

7-Methoxy-3-(1-methyl-2-phenylethyl)-1,2,4,5-tetrahydro-3H,3-benzazepine hydrochloride (13.0 gm., 0.039 1 m) was suspended in 48% aqueous hydrobromic acid (180 ml.) and refluxed with vigorous stirring for 7 hours. The cooled reaction mixture was filtered and the precipitate was washed with water and actone. m.p. 240°–250°. wt.=13.5. gm. The solid was dissolved in dimethylformamide:water (50 ml:1 l.) and sodium hydroxide solution (50%, 3.12 gm.) was added. The precipitated gum was extracted into chloroform and the chloroform solution was dried over magnesium sulfate. Evaporation of the chloroform in vacuo afforded the title compound as an oil. The amine was converted to the hydrochloride salt and recrystallized from methanol m.p. 273°–283° (d). wt.=8 gm.

Anal. Calc. for $C_{19}H_{23}NO \cdot HCl$: C, 71.80; H, 7.61; N, 4.41; Cl, 11.16. Found: C, 72.09; H, 7.78; N, 4.71; Cl, 11.17.

EXAMPLE 28

7-Methoxy-3-(3-phenylallyl)-1,2,4,5-tetrahydro-3H,3-benzazepine (Method A)

7-Methoxy-1,2,4,5-tetrahydro-3H,3-benzazepine (10 gm., 0.0564 m). triethylamine (5.65 gm, 0.0564 m), dimethylformamide (20 ml.) and benzene (80 ml.) were mixed and stirred at room temperature. A solution of 3-chloropropenylbenzene (8.6 gm., 0.0564 m) in benzene (30 ml.) was added dropwise during 5 minutes. The reaction was stirred for 4 hours and then water (200 ml.) was added. The benzene layer was separated and washed with water. After drying over magnesium sulfate the benzene was evaporated in vacuo to give an oil. The oil was purified by chromatography on silica gel and elution with benzene:methanol (4:1) The pure amine (10.1 gm.) was converted to the hydrochloride salt and recrystallized from methylethylketone:methanol (15:1). m.p. 198°–200°. wt.=9.4 gm.

Anal. Calc. for $C_{20}H_{23}NO \cdot HCl$: C, 72.81, H, 7.33; N, 4.25; Cl, 10.75. Found: C, 72.79; H, 7.39; N, 4.20; Cl, 10.84.

EXAMPLE 29

7-Hydroxy-3-(3-phenylallyl)-1,2,4,5-tetrahydro-3H,3-benzazepine (Method C)

Triethylamine (8.15 gm., 0.082 m) was added to a solution of 7-hydroxy-1,2,4,5-tetrahydro-3H,3-benzazepine hydrobromide (10 gm., 0.041 m) in dimethylformamide (35 ml.). After 5 minutes 3-chloropropenylbenzene (6.25 gm., 0.041 m). was added dropwise during 15 minutes. The reaction was stirred at room temperature for 4 hours. Water was added and the product was isolated by extraction into ethyl acetate. The ethyl acetate extract was dried over magnesium sulfate and then the solvent was evaporated in vacuo to give the title compound as a solid which was recrystallized from diisopropyl ether:methanol (5:1). m.p. 158°–159°, wt.=8.1 gm.

Anal. Calc. for $C_{19}H_{21}NO$:- C, 81.68, H, 7.58; N, 5.01 Found: C, 81.63; N, 7.87; N, 5.28.

EXAMPLE 30

7-Hydroxy-3(trans-2-phenylcyclopropylmethyl)-1,2,4,5-tetrahydro-3H,3-benzazepine (Method D)

Triethylamine (15.5 gm., 0.154 m) was added to a solution of 7-hydroxy-1,2,4,5-tetrahydro-3H,3-benzazepine hydrobromide (12.5 gm., 0.0512 m) in dimethylformamide (100 ml.) which was being stirred at room temperature. After 5 minutes, trans-2-phenylcyclopropane carboxylic acid chloride (18.45 gm., 0.0124 m) was added dropwise during 20 minutes. The reaction was stirred at room temperature for 3 hours. The reaction mixture was diluted with ethyl acetate (400 ml.) and water (200 ml.). The ethyl acetate extract was washed with hydrochloric acid (3N) and sodium bicarbonate solution. The ethyl acetate layer was dried over magnesium sulfate and evaporated in vacuo to give a gum. wt.=18 gm. This material was dissolved in tetrahydrofuran (100 ml.) and the solution was added dropwise to a suspension of lithium aluminum hydride (3.9 gm., 0.1024 m) in tetrahydrofuran (100 ml.) during 30 minutes at room temperature. The reaction was stirred at room temperature for 3 hours. Ethyl acetate (15 ml.) was added cautiously followed by a saturated aqueous solution of ammonium tartrate (200 ml.). The tetrahydrofuran layer was separated and evaporated in vacuo. The residue was dried by

EXAMPLE 31

7-Methoxy-3-[2-(4-phenyl-1-piperazinyl) ethyl]-1,2,4,5-tetrahydro-3H,3-benzazepine A solution of 2-(4-phenyl-1-piperazinyl) ethyl chloride (16.5 gm., 0.074 m) in benzene (50 ml.) was added dropwise during 30 minutes to a solution of 7-methoxy-1,2,4,5-tetrahydro-3H,3-benzazepine (11.9 gm., 0.067 m), triethylamine (7.5 gm., 0.074 m) and dimethylformamide (30 ml.) in benzene (90 ml.) at room temperature. The reaction was stirred at room temperature for 6 hours and then at reflux for 24 hours. The cooled reaction was diluted with water and the benzene layer was separated, dried over magnesium sulfate and evaporated in vacuo. The residual oil solidified and the solid was crystallized from isopropanol to give the title compound. m.p.=103°–4°. wt.=9.2 gm.

The amine was converted to the dihydrochloride salt in methanol solution and was recrystallized from methanol. m.p.=282°–6° (d).

Anal. Calc. for $C_{23}H_{31}N_3O\cdot 2HCl$: C, 61.94; H, 7.65; N, 9.43; Cl, 15.91. Found: C, 62.16 H, 7.88; N, 9.64; Cl, 15.92.

ALKYL SUBSTITUTION ON THE AZEPINE RING

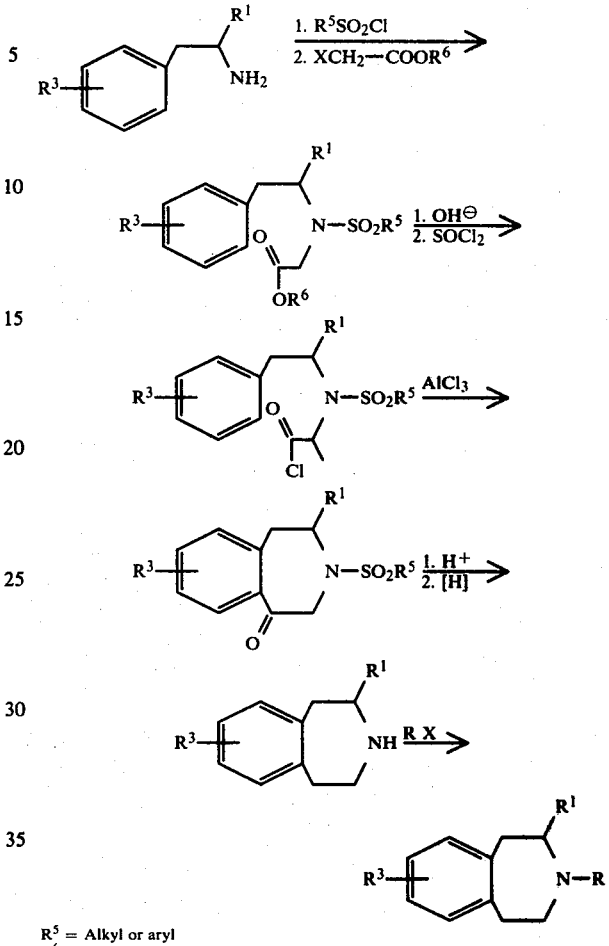

$R^5$ = Alkyl or aryl
$R^6$ = hydrocarbon
X = halogen

EXAMPLE 32

8-Methoxy-2-methyl-1,2,4,5-tetrahydro-3H,3-benzazepine

7-Methoxy-4-methyl-3-toluene-p-sulfonyl-1,2,4,5-tetrahydro-3H,3-benzazepine-1-one A solution of p-toluenesulfonyl chloride (28.0 gm., 0.15 M) in benzene (100 ml.) was added dropwise to a solution of 2-(3-methoxyphenyl)-1-methylethylamine (23 gm., 0.139 M) and triethylamine (13 gm., 0.15 M) in benzene (200 ml.) during 30 minutes. The reaction was stirred at room temperature for 4 hours. The precipitated triethylamine hydrochloride was filtered off and the benzene solution was washed with hydrochloric acid (3N), water and saturated brine. The benzene solution was dried over magnesium sulfate. Evaporation of the solvent afforded N-toluene-p-sulfonyl-2-(3-methoxyphenyl)-1-methylethylamine as an oil Wt=42 gm.

The crude sulfonamide (43 gm., 0.135 M) was dissolved in acetone (1100 ml.). Anhydrous potassium carbonate powder (135 gm.) was added and the reaction was stirred and refluxed. Ethylbromoacetate (33.7 gm., 0.202 M) was added in four equal portions at 30 minute intervals. After stirring and refluxing for 20 hours the salts were filtered from the cooled solution. Evaporation of the acetone gave an oily residue which consisted mainly of the alkylated amine. The ester function was hydrolyzed by refluxing the oil with ethanol (95%, 900 ml.) and sodium hydroxide (10% aqueous, 270 ml.) for 6 hours. The ethanol was removed on the rotary evaporator and the aqueous residue was diluted with water (1 l.) until a clear solution was obtained. The solution was washed with diethyl ether and then it was made acid with concentrated hydrochloric acid. The oily precipitate was extracted into ether and then the ether solution was washed with sodium bicarbonate solution. The bicarbonate solution was separated and acidified with concentrated hydrochloric acid and the precipitated acid was isolated in diethyl ether. The ether solution was dried over magnesium sulfate. Evaporation of the solvent afforded N-[2-(3-methoxyphenyl)-1-methyl]ethyl-N-toluene-p-sulfonyl glycine as a viscous oil which resisted crystallization. Wt=40.5 gm.

The crude acid (40 gm., 0.106 M) was refluxed in benzene solution (500 ml.) with thionyl chloride (25.3 gm., 0.212 M) for 9 hours. The excess thionyl chloride and solvent were removed on the rotatory evaporator. The crude acid choloride was dissolved in methylene dichloride (100 ml.) and added dropwise to a suspension of aluminum chloride (17.4 gm., 0.13 M) in methylene dichloride (300 ml.) which had been cooled to $-65°$ C. The addition took 3 hours. The reaction was stirred at $-65°$ for 7 hours and then it was stirred while warming to 15° C. during 12 hours. The reaction mixture was poured onto ice (1500 gm.)/concentrated hydrochloric acid (75 ml.) and the mixture was stirred for 1.5 hours. The methylene chloride layer was separated and washed with water, sodium bicarbonate solution and saturated brine. Evaporation of the solvent afforded an oil. Wt=37 gm. The oil was purified by chromatography on silica gel. Elution of the column with acetone:-benzene (1:40) afforded the crude title compound which was purified by crystallization from absolute methanol. Wt=11.4 gm. m.p. 119°-121.5°.

Anal. Calcd. for $C_{19}N_{21}NO_4S$: C, 63.49; N, 5.89; N, 3.90; S, 8.92 Found: C, 63.77; N, 6.04; N, 3.61; S, 8.93

1-Hydroxy-7-methoxy-4-methyl-3-toluene-p-sulfonyl-1,2,4,5-tetrahydro-3H,3-benzazepine Sodium borohydride (1 gm., 0.0264 M) was added during 5 minutes to a suspension of 7-methoxy-4-methyl-3-toluene-p-sulfonyl-1,2,4,5-tetrahydro-3H,3-benzazepin-1-one (7.5 gm., 0.0208 M) in absolute ethanol (100 ml.) at room temperature. The mixture was warmed to 60° during 30 minutes and then the heat source was removed. After stirring for a further 3 hours at room temperature the reaction mixture was poured onto ice/concentrated hydrochloric acid (500 ml./25 ml.). The precipitate was extracted into chloroform. Evaporation of the chloroform afforded a viscous oil which, on trituration with diethyl ether afforded a solid. Wt=5.4 gm. m.p.=83°-87°. The solid was crystallized from diethyl ether to give the pure title compound. m.p. 84°-87°.

Anal. Calcd. for $C_{19}H_{23}NO_4S$: C, 63.14; H, 6.41; N, 3.88; S, 8.87 Found: C, 63.09; H, 6.40; N, 4.00; S, 9.11

8-Methoxy-2-methyl-3-toluene-p-sulfonyl-1,2-dihydro-3H,3-benzazepine

1-Hydroxy-7-methoxy-4-methyl-3-toluene-p-sulfonyl-1,2,4,5-tetrahydro-3H,3-benzazepine (7 gm., 0.0194 M) and p-toluene sulfonic acid (20 mg.) were dissolved in benzene (80 ml.) and the solution was refluxed for 1.5 hours. The solvent was condensed over a Soxhlet tube containing Linde Type 3A molecular sieves (1/16"). The solvent was evaporated and the residue was purified by chromatography on silica gel. Elution of the column with acetone:benzene (3:100) afforded an oil which solidified on trituration with diisopropyl ether to give the title compound. Wt=5.0 gm. m.p.=77°-79°

Anal. Calcd. for $C_{19}H_{21}NO_3S$: C, 66.43; H, 6.16; N, 4.08; S, 9.34 Found: C, 66.26; N, 6.28; N, 3.93; S, 9.23

Further elution of the column afforded a solid which was crystallized from absolute methanol. Wt=0.38 gm. m.p.=177°-182°

Found: C, 66.20; H, 6.38; N, 3.95; S, 9.52

8-Methoxy-2-methyl-3-toluene-p-sulfonyl-1,2,4,5-tetrahydro-3H,3-benzazepine

A solution of 8-methoxy-2-methyl-3-toluene-p-sulfonyl-1,2-dihydro-3H,3-benzazepine (4.7 gm., 0.0137 M) in acetic acid (30 ml.) was hydrogenated over 5% palladium-charcoal (0.4 gm.) in a Parr apparatus at an initial pressure of 37 p.s.i. The adsorption of hydrogen was complete in 2.5 hours. The catalyst was filtered off and the filtrate was evaporated to dryness. The residue was triturated with diisopropyl ethyl to give the title compound as a solid. Wt=4.3 gm. The solid was crystallized from absolute methanol. m.p.=86°-89°

Anal. Calcd. for $C_{19}H_{23}NO_3S$: C, 66.07; H, 6.71; N, 4.06; S, 9.28 Found: C, 66.10; H, 6.88; N, 3.97; S, 9.29

8-Methoxy-2-methyl-1,2,4,5-tetrahydro-3H,3-benzazepine

8-Methoxy-2-methyl-3-toluene-p-sulfonyl-1,2,4,5-tetrahydro-3H,3-benzazepine (1 gm., 0.003 M) was susepnded in liquid ammonia (35 ml.). Sodium (0.15 gm.) was added portionwise until the blue color persisted. After a further 15 minutes ammonium chloride (2 gm.) was added and the ammonia was allowed to evaporate. Water was added and the insolubles were extracted into diethyl ether. Evaporation of the ether afforded an oil, Wt=0.62 gm. The title compound was isolated as the hydrochloride salt and the salt was crystallized from iso-propanol. Wt=0.28 mg. m.p.=196°-200°. Anal. Calcd. for $C_{12}H_{17}NO.HCl$ : C, 63,29; H, 7.97; Cl, 15.57; N, 6.15 Found: C, 63.34; H, 8.22; Cl, 1, 15.33; N, 6.20

The precursors for 8-methoxy-2-methyl-1,2,4,5-tetrahydro-3H,3 -benzazepines and other compounds of this invention can also be prepared as follows:

N-Methanesulfonyl-2-(3-methoxypheryl)-1-methylethylamine

Methanesulfonyl chloride (131 g, 1.15 M) was added during 30 min. to a solution of 2-(3-methoxyphenyl)-1-methylethylamine (189.7 g, 1.15 M) and triethylamine (116.7 g, 1.15 M) in benzene (2 l) with cooling to maintain an internal temperature of 20°-30°. The reaction was stirred at room temperature for 2 hr. The benzene solution was filtered from the triethylamine hydrochloride. The filter cake was washed with benzene (500 ml) and the combined filtrates were washed with 1 N.HCl (2×250 ml) and water (2×250 ml). The solution was dried over magnesium sulfate and then evaporated to give the sulfonamide as a thick oil. Wt=292 g.

N-Methanesulfonyl-N-[2-(3-methoxyphenyl)-1-methylethyl]-glycine

Ethyl bromoacetate (266 g, 1.23 M) was added in four equal portions at 30 min. intervals to a stirred, refluxing suspension of N-methanesulfonyl -2-(3-methoxyphenyl)-1-methylethylamine (292 g, 1.2 M) and potassium carbonate (anhydrous, freshly ground) (1,066 g, 7.7 M) in acetone (7 l) under a nitrogen atmosphere. The reaction was stirred and refluxed for 24 hr. The salts were filtered and the filter cake was washed with acetone (2 l). The filtrate was evaporated on a rotatory evaporator at 15 mm. The residual ester was hydrolyzed by dissolving it in 95% ethyl alcohol (4 l) and adding 10% aqueous sodium hydroxide solution (1.1 l) and refluxing the solution for 4 hr. The ethyl alcohol was evaporated on a rotatory evaporator at 15 mm and the aqueous residue was diluted with water (4 l) to give a clear solution. The acid was precipitated by adding excess hydrochloric acid (conc) to the ice-cooled solution of the sodium salt. The precipitated oil was extracted into ethyl acetate (3×600 ml). The carboxylic acid was extracted from the ethyl acetate with saturated sodium carbonate solution. The carbonate extract was acidified with 6N.HCl and the precipitated acid was isolated in ethyl acetate (3×600 ml). The ethyl acetate solution was dried over magnesium sulfate and evaporated to give the title compound as a gum which slowly solidifies. Wt=350 g. mp=100°-101° (from benzene).

3-Methanesulfonyl-7-methoxy-4-methyl-1,2,4,5-tetrahydro-3H,3-benzazepin-1-one N-Methanesulfonyl-N-[2-(3-methoxyphenyl)-1methylethyl]to glycine (279 g. 0.92 M), thionyl chloride (251 g, 2.1 M) and benzene (3 l) were refluxed together for 4 hr. The solent and excess thionyl chloride were evaporated on the rotatory evaporator at 15 mm. The residue was redissolved in benzene (500 ml) and evaporated to dryness again. The final traces of thionyl chloride were removed by evaporating for 30 min. at 70°/0.5 mm. The product is thick oil. The crude acid chloride was dissolved in methylene chloride (1 l) and added dropwise during 2 hr to a stirred suspension of aluminum chloride (257 g, 1.93 M) in methylene chloride (1.2 l) at 0° C. under a nitrogen atmosphere. The reaction was then stirred to room temperature for 4 hr. The reaction mixture was poured into a vigorously stirred ice-water (10 l)/concentrated hydrochloric acid (500 ml) mixture and after 30 min the methylene chloride layer was separated. The equeous layer was extracted with two 1 l portions of methylene chloride and the combined extracts were washed wth water (3×500 ml) and dried over magnesium sulfate. Evaporation of the solvent on a rotatory evaporator at 15 mm afforded a semi-solid. This residue was triturated with methanol (400 ml) at room temperature. The insoluble ketone was filtered. mp 147°-150 °, Wt=128 g.

1-Hydroxy-3-methanesulfonyl-7-methoxy-4-methyl-1,2,4,5-tetrahydro-3H,3-benzazepine 3-Methanesulfonyl-7-methoxy-4-methyl-1,2,4,5-tetrahydro-3H,3-benzazepin-1-one (66.4 g, 0.234 M) was suspended in 95% ethanol (1900ml) at room temperature. Sodium borohydride (10.8 g, 0.285 M) was added portionwise as rapidly as possible without excessive foaming occurring. The reaction was stirred for 1 hr. at room temperature and then poured into ice-water (10 l)/concentrated hydrochloric acid (300 ml). The precipitated oil was extracted into chloroform (3×1200 ml). The chloroform layer was eashed with water (3×500 ml) and dried over magnesium sulfate. The solvent was evaporated on a rotatory evaporator at 15 mm to give the alcohol as an oil which solidified. Wt=72 g, mp 104°-6° (from iso-propanol).

3-Methanesulfonyl-8-methoxy-2-methyl-1,2-dihydro-3H,3-benzazepine

1-Hydroxy-3-methanesulfonyl-7-methoxy-4-methyl-1,2,4,5-tetrahydro-3-H,3-benzazepine (70 g, 0.246 M) was dissolved in dimethyl sulfoxide (200 ml) and concentrated sulfuric acid (0.5 ml) was added. The raction was stirred at 100° C. for 5 hr. The reaction mixture was poured into water (1200 ml) and the precipitated oil was extracted into benzene (3×500 ml). The benzene layer was eashed with water (3×300 ml) and dried over magnesium sulfate. The solvent was evaporated on a rotary evaporator at 15 mm to give the title compound as a solid. Trituration with iso-propanol (150 ml) and filtration of the insoluble material gave the title compound. mp 110°-112° (from iso-propanol), Wt=42 g.

3-Methanesulfonyl-8-methoxy-2-methyl-1,2,4,5-tetrahydro-3-H,3-benzazepine

3-Methanesulfonyl-8-methoxy-2-methyl-1,2-dihydro-3H,3-benzazepine (83 g, 0.291 M) was suspended in acetic acid (1 l) and 5% palladium/charcoal (3 g) was added. The reaction mixture was reduced on a Parr hydrogenator at 50 p.s.i. until the adsorption of hydrogen ceased.

The catalyst was filtered and the solvent was evaporated on a rotatory evaporator at 15 mm to give the title compound as a solid. The solid was washed with iso-propanol and filtered. Wt=65 g. mp 90°-92° (from iso-propanol).

The 3-methanesulfonyl-7-methoxy-4-methyl-1,2,4,5-tetrahydro-3H,3-benzazipin-1-one may be converted to the 3-methanesulfonyl-8-methoxy-2-methyl-1,2,4,5-tetrahydro-3H,3-benzazepine as follows:

3-Methanesulfonyl-8-methoxy-2-methyl-1,2,4,5-tetrahydro-3H,3-benzazepine

3-Methanesulfonyl-7-methoxy-4-methyl-1,2,4,5-tetrahydro-3H,3-benzazepine-1-one (100 gms. 0.35 M) was suspended in acetic acid/conc HCl (1l/16 ml) and reduced over 5% palladium charcoal (10 gms). The reaction mixture was reduced on a Parr hydrogenator at 50 p.s.i. until the adsorption of hydrogen ceased. (50 lbs; theory 50.6lbs.).

The catalyst was filtered and the solvent was evaporated on a rotatory evaporator at 15 mm to give the title compound which was treated with n-butanol (100 ml) filtered and washed with n-butanol (30 ml) to give 865 gms. m.pt.=90°-92°.

8-Methoxy-2-methyl-1,2,4,5-tetrahydro-3H,3-benzazepine

3-Methanesulfonyl-8-methoxy-2-methyl-1,2,4,5-tetrahydro-3H,3-benzazepine (365 gms, 1.36 M) was dissolved in benzene (1800 ml)and added to a solution of Red-Al(1519 gms of a 70% solution in benzene=5.70 M) in benzene (3.7 l) at 50° C. during 30 min. The temperature was maintained at 50°-55° C. for 20 hrs. After cooling the reaction mixture to 15° C., sodium hydroxide solution (10%, 1475 ml) was added slowly and then the benzene layer was separated. The benzene layer was washed with water (2 l) and then with 6N.HCl (3×1200 ml). The acid layer was basified with sodium hydroxide (50%) and the precipitated oil was extracted into benzene (1×2 l, 2×1 l). The combined extracts were dried over MgSO4 and evaporated to give the crude amine.

The amine was distilled at 90° C./0.025 mm to give 217.5 gms.

EXAMPLE 33

3-(3,3-Dimethylallyl)-8-methoxy-2-methyl-1,2,4,5-tetrahydro-3H,3-benzazepine hydrochloride (778–030)

8-Methoxy-2-methyl-1,2,4,5-tetrahydro-3H,-3-benzazepine (12 g) and 8.9 ml triethylamine were dissolved in 100 ml benzene and 20 ml dimethylformamide at room temperature. A solution of 6.6 g 1-chloro-3-methyl-2-butene in 20 ml benzene-dimethylformamide was added dropwise during ½ hr. After 24 hrs the mixture was filtered and diluted with water. The benzene layer was washed with water and brine to give 14.7 g of an oil. The oil was chromatographed on silica and the product dissolved in ether and treated with HCl gas. The gummy salt was treated with warm tetrahydrofuran to give 6.5 g product, m. 165°–8°.

|   | Calcd | Found |
|---|-------|-------|
| C | 69.02 | 69.11 |
| H | 8.85  | 8.76  |
| Cl| 11.98 | 12.09 |
| N | 4.73  | 4.58  |

EXAMPLE 34

3-(3,3-Dimethylallyl)-8-hydroxy-2-methyl-1,2,4,5-tetrahydro-3H,3-benzazepine hydrochloride (778–016)

Step 1.
8-Hydroxy-2-methyl-1,2,4,5-tetrahydro-3H,3-benzazepine hydrobromide

8-Methoxy-2-methyl-1,2,4,5-tetrahydro-3H,3-benzazepine (10 g) was refluxed 4 hrs with 100 ml 48% HBr. The mixture was concentrated on the rotovap to a solid which was washed with acetone and filtered to give 11.5 g product, m. 220°–2°. A portion of the salt was converted to base which was recrystallized from isopropanol to give a solid, m. 208°–10°.

|   | Calcd | Found |
|---|-------|-------|
| C | 74.54 | 74.67 |
| H | 8.53  | 8.64  |
| N | 7.90  | 7.53  |

Step. 2.
3-(3,3-Dimethylallyl)-8-hydroxy-2-methyl-1,2,4,5-tetrahydro-3H,3-benzazepine hydrochloride 8-Hydroxy-2-methyl-1,2,4,5-tetrahydro-3H,3-benzazepine hydrobromide (11 g) was dissolved in 50 ml dimethylformamide and 8.6 g triethylamine added. 1-Chloro-3-methyl-2-butene (1.1 equivalent) was added during 15 min at 10°. After 3 to 5 hrs at room temperature, the reaction was poured into 300 ml water and extracted with ethyl acetate. The ethyl acetate extract was dried and concentrated to dryness to give 6 g solid which was chromatographed on silica to give 5.5 g solid. This was dissolved in methanol and treated with methanolic HCl to give the hydrochloride which was recrystallized from methanol-ether to give 4.2 g product, m. 203°–6°.

|   | Calcd | Found |
|---|-------|-------|
| C | 68.19 | 67.81 |
| H | 8.58  | 8.44  |
| Cl| 12.58 | 12.36 |
| N | 4.97  | 4.73  |

EXAMPLE 35

3-(3,3-Dimethylallyl)-6-hydroxy-2-methyl-1,2,4,5-tetrahydro-3H,3-benzazepine hdrochloride (786–726)

During the purification of 7-methoxy-4-methyl-3-toluene-p-sulfonyl-1,2,4,5-tetrahydro-3H,3-benzazepin-1-one (intermediate in example 30), some of the 9-methoxy isomer was isolated as a by-product. The 9-methoxy compound was used to prepare 6-methoxy-2-methyl-1,2,4,5-tetrahydro-3H,3-benzazepine following the method used for the preparation of 8-methoxy-2-methyl-1,2,4,5-tetrahydro-3H,3-benzazepine from 7-methoxy-4-methyl-3-toluene-p-sulfonyl-1,2,4,5-tetrahydro-3H,3-benzazepin-1-one shown in example 30. Hydrolysis of 6-methoxy-2-methyl-1,2,4,5-tetrahydro-3H,3-benzazepine with 48% HBr gave 6-hydroxy-2-methyl-1,2,4,5-tetrahydro-3H,3-benazazepine hydrobromide.

6-Hyroxy-2-methyl-1,2,4,5-tetrahydro-3H,3-benzazepine hydrobromide (7.2 g), 3.03 g of 1-chloro-3-methyl-2-butene, 15 g of anhydrous Na$_2$CO$_3$, and 50 ml butanol were stirred 3 hrs at 50°. The mixture was filtered, the filtrate concentrated to dryness, and the residue chromatographed on silica. The product was triturated with tetrohydrofuran to give a solid which was suspended in tetrahydrofuran containing HCl gas, filtered, and dried at 90° under a high vacuum to give solid m. 180°–5°. The product was recrystallized from isopropanol, dissolved in water, treated with NaOH, extracted into chloroform and the chloroform taken off. The residue was dissolved in methanol and treated with HCl gas to give the HCl salt which was recrystallized from isopropanol and dried at 90° to give 0.7 g of product, m. 174°–8°.

|   | Calcd | Found |
|---|-------|-------|
| C | 68.19 | 68.42 |
| H | 8.58  | 8.46  |
| Cl| 12.58 | 12.47 |
| N | 4.97  | 4.94  |

EXAMPLE 36

8-Methoxy-2-methyl-3-phenethyl-1,2,4,5-tetrahydro-3H,3-benzazepine hydrochloride 8-Methoxy-2-methyl-1,2,4,5-tetrahydro-3H,3-benzazepine (10 g.) and 5.4 g. triethylamine were stirred in 100 ml. chloroform at room temperature. Phenylacetyl chloride (8.3 g.) was added dropwise over 15 minutes and the mixture stirred for five hours. The solution was washed with dilute HCl, water, and brine, dried and concentrated. The residual oil was dissolved in 100 ml. tetrahydrofuran and the solution added dropwise over one hour to a cooled suspension of 2 g. LiAlH$_4$ in 100 ml. tetrahydrofuran. The reaction was refluxed two hours, added 2 ml. water, 2 ml. 15% NaOH and 6 ml. water and filtered. The filtrate was dried and concentrated to give an oil which was dissolved in ether and treated with dry HCl to give the hydrochloride. The product was recrystallized from 200 ml. iospropanol and then from 100 ml. isopropanol to give 5.9 g. product.

|        | C     | H    | N    | Cl    |
|--------|-------|------|------|-------|
| Calcd. | 72.38 | 7.90 | 4.22 | 10.68 |
| Found  | 72.44 | 7.76 | 4.24 | 10.73 |

EXAMPLE 37

3-Cyclopropylmethyl-1,2,4,5-tetrahydro-3H,3-benzazepine hydrochloride

Step 1: 3-Cyclopropylcarbonyl-1,2,4,5-tetrahydro-3H,3-benzazepine.

1,2,4,5-Tetrahydro-3H,3-benzazepine (8.14 g) was dissolved in 50 ml. tetrahydrofuran containing 5 ml. pyridine.

The solution was cooled, 6.5 g. cyclopropyl carboxylic acid chloride in 50 ml tetrahydrofuran added over ½ hour and the mixture stirred 4 hrs. Water (100 ml.) was added and the tetrahydrofuran removed by concentration under vacuum. The aqueous mixture was extracted with ether and the ether extract washed with dilute NaOH and dilute HCl and dried to give 8 g. product, m. 65-8.

Step 2: 3-Cyclopropylmethyl-1,2,4,5-tetrahydro-3H,3-benzazepine hydrochloride.

3-Cyclopropylcarbonyl-1,2,4,5-tetrahydro-3H,3-benzazepine (11.3 g.) was dissolved in 80 ml. tetrahydrofuran and the slution added dropwise over 1½ hrs to a refluxing suspension of 2.8 g. LiAlH₄ in 250 ml. tetrahydrofuran. The reaction was refluxed overnight, cooled, treated with 2.8 ml. 15% NaOH and 8.4 ml. water. The solution was filtered, dried and concentrated to an oil which was dissolved in ether and treated with a solution of HCl gas in ether. The solid was filtered and recrystallized from acetonitrile to give 7.7 g., m. 255-7.

|        | C     | H    | N    | Cl    |
|--------|-------|------|------|-------|
| Calcd. | 70.73 | 8.48 | 5.89 | 14.91 |
| Found  | 70.47 | 8.39 | 5.80 | 14.89 |

EXAMPLE 38

3-Allyl-8-methoxy-2-methyl-1,2,4,5-tetrahydro-3H,3-benzazepine hydrochloride

8-Methoxy-2-methyl-1,2,4,5-tetrahydro-3H,3-benzazepine (7 g.+5 g. HCl) were dissolved in 25 ml. dimethylformamide and 11.2 ml. triethylamine added. Benzene (100 ml.) was added and the mixture stirred for 10 minutes. A solution of 7.1 g. 3-bromopropene in 50 ml. benzene was added dropwise over 15 minutes to the ice-cooled reaction. The reaction was stirred four hours at room temperature, poured into 300 ml. water and the benzene layer separated and concentrated to give an oil which was chromatographed on silica to give the base. This was dissolved in ether and treated with HCl to give the hydrochloride which was recrystallized from 75 ml. propanol to give 6.25 g. product.

|        | C     | H    | N    | Cl    |
|--------|-------|------|------|-------|
| Calcd. | 67.28 | 8.28 | 5.23 | 13.24 |
| Found  | 67.14 | 8.29 | 5.10 | 13.18 |

EXAMPLE 39

8-Methoxy-2,3-dimethyl-1,2,4,5-tetrahydro-3H,3-benzazepine hydrochloride

8-Methoxy-2-methyl-1,2,4,5-tetrahydro-3H,3-benzazepine (10 g.) was refluxed six hours with 24 ml. formalin and 28 ml. formic acid. The mixture was concentrated and the residue dissolved in water, made alkaline with dilute NaOH and extracted with benzene. The benzene was concentrated to give an oil which was converted to the hydrochloride in ether. The gummy precipitate was warmed with ether acetate to give a solid salt which was recrystallized from butanol to give 9 g. product, m. 196-8.

|        | C     | H    | N    | Cl    |
|--------|-------|------|------|-------|
| Calcd. | 64.59 | 8.34 | 5.79 | 14.66 |
| Found  | 64.42 | 8.22 | 5.65 | 14.27 |

EXAMPLE 40

8-Methoxy-2-methyl-3-[2-(4-phenyl-1-piperazinyl)-ethyl]-1,2,4,5-tetrahydro-3H,3-benzazepine dihydrochloride 8Methoxy-2-methyl-1,2,4,5-tetrahydro-3H,3-benzazepine (21.1 g.) and 18.4 ml. triethylamine in 66 ml. dimethylformamide were treated with 29.3 g. 1-(2-chloroethyl)-4-phenylpiperazine in 75 ml. dimethylformamide. The mixture was heated 21 hours at 90°, cooled, poured into 1300 ml. water and extracted with chloroform. The chloroform extract was washed with water, dried and concentrated. The residue was taken up in either and treated with dry HCl to give a solid which was recrystallized twice from absolute ethanol to give 17.5 g. product, m. 255-60 (dec.).

|        | C     | H    | N    | Cl    |
|--------|-------|------|------|-------|
| Calcd. | 62.98 | 7.86 | 9.18 | 15.25 |
| Found  | 63.09 | 8.16 | 9.31 | 15.20 |

EXAMPLE 41

3-Cyclopropylmethyl-8-hydroxy-2-methyl-1,2,4,5-tetrahydro-3H,3-benzezepine hydrochloride (807-607)

3,8Dicyclopropylcarbonyl-2-methyl-1,2,4,5-tetrahydro-3H,3-benzazepine 8-Hydroxy-2-methyl-1,2,4,5-tetrahydro-3H,3-benzazepine hydrobromide (17.4 g.) was dissolved in 56.5 dimethylformamide and 31.3 ml triethylamine. Cyclopropanecarboxylic acid chloride (17.4 ml) was added dropwise to the solution which was cooled in an ice bath. The mixture was stirred 2½ hrs at room temperature, 120 ml water added and the mixture extracted with ethyl acetate. The ethyl acetate extract was washed with dilute HCl, NaHCO₃ solution, water and saturated NaCl, dried and concentrated to dryness to give 22.4 g residue which was used in the next step without further purification.

3-Cyclopropylmethyl-8-hydroxy-2-methyl-1,2,4,5-tetrahydro-3H,3-benzazepine 3,8-Dicyclopropylcarbonyl-2-methyl-1,2,4,5-tetrahydro-3H,3-benzazepine (22.4 g) was dissolved in 236 ml dry tetrahydrofuran and the solution added dropwise to a suspension of 5.9 g LiAlH$_4$ ml tetrahydrofuran at room temperature. The reaction mixture was stirred 18 hrs, 59 ml ethyl acetate added dropwise followed by a solution of 389 g ammonium tartrate in 885 ml water. After stirring for 1 hour, the organic layer was separated and concentrated to dryness. The residue was taken up in chloroform, washed with water, dried, and concentrated to dryness to give an oil which was dissolved in a minimum amount of tetrahydrofuran and diluted with twice the volume of ether. The solution was treated with HCl gas and the solid filtered and recrystallized from propanol to give 13.8 g product, m. 209°–12°.

|    | Calcd | Found |
|----|-------|-------|
| C  | 67.28 | 67.14 |
| H  | 8.28  | 8.34  |
| Cl | 13.24 | 13.19 |
| N  | 5.23  | 5.18  |

EXAMPLE 42

3-Cyclopropylmethyl-8-methoxy-2-methyl-1,2,4,5-tetrahydro-3H,3-benzazepine hydrochloride (795–209)

8-Methoxy-2-methyl-1,2,4,5-tetrahydro-3H,3-benzazepine hydrochloride (15 g.) was stirred 15 minutes with 20 ml. dimethylformamide and 14.1 g. triethylamine, 80 ml. benzene added and a solution of 7.3 g. cyclopropane carboxylic acid chloride in 20 ml. benzene added dropwise over 30 minutes at 20°–40°. After four hours at room temperature, the reaction was poured into 300 ml. water and the benzene layer separated, washed with water, dilute HCl, and water. The benzene solution was dried and concentrated and the residue dissolved in 150 ml. tetrahydrofuran and added to 3 g. LiAlH$_4$ in 400 ml. tetrahydrofuran over 30 minutes at reflux. The reaction was refluxed four hours, treated with water. The organic layer gave an oil which was converted to the hydrochloride in ether. The gummy precipitate was treated with warm tetrahydrofuran and recrystallized from 200 ml. acetone to give 7.7 g., m. 150–5.

|       | C     | H    | N    | Cl    |
|-------|-------|------|------|-------|
| Calcd.| 68.19 | 8.58 | 4.97 | 12.58 |
| Found | 68.67 | 8.59 | 4.57 | 12.80 |

EXAMPLE 43

3-(3',3'-Dimethylallyl)-1,2,4,5-tetrahydro-3H,3-benzazepine hydrochloride (654–096)

1,2,4,5-Tetrahydro-3H,3benzazepine (20 g.) was added to 14.2 g. 1-chloro-3-methyl-but-2-ene at room temperature, the mixture heated two hours at 50°, dissolved in a mixture of water, NaOH and ether. The ether layer was separated, dried and concentrated to an oil which was distilled. The fraction b. 90–2 at 0.15 mm. was converted to the hydrochloride with an ether solution of HCl. The HCl salt was recrystallized from alcohol to give 11.5 g., m. 242–3.

|       | C     | H    | N    | Cl    |
|-------|-------|------|------|-------|
| Calcd.| 71.57 | 8.80 | 5.56 | 14.08 |
| Found | 71.43 | 8.79 | 5.54 | 14.06 |

EXAMPLE 44

8-Methoxy-2-methyl-3-(3-phenylallyl)-1,2,4,5-tetrahydro-3H,3-benzazepine hydrochloride (786–796)

8-Methoxy-2-methyl-1,2,4,5-tetrahydro-3H,3-benzazepine (10 g.), 5.3 g. triethylamine, 20 ml. dimethylformamide, and 80 ml. benzene were mixed and stirred at room temperature. 3-Chloropropenylbenzene (8.1 g.) was added dropwise over 15 minutes. The reaction was stirred two hours at room temperature, heated 16 hours at 75° and water added. The benzene layer was separated, dried and evaporated to an oil. The oil solidified and was triturated with heptane to give 8 g. solid which was dissolved in ether and converted to the hydrochloride. The HCl salt was recrystallized from isopropanol-ether to give 6.2 g. product.

|       | C     | H    | N    | Cl    |
|-------|-------|------|------|-------|
| Calcd.| 73.34 | 7.62 | 4.07 | 10.31 |
| Found | 73.15 | 7.37 | 3.91 | 10.45 |

EXAMPLE 45

3-(4-Acetoxyethyl)-7-methoxy-1,2,4,5-tetrahydro-3H,3-benzazepine

7-Methoxy-1,2,4,5-tetrahydro-3H,3-benzazepine (12 gm. 0.068 m) and ethylene oxide (4 gm., 0.091 m) were dissolved in methanol at −40° C. The solution was stirred as the temperature rose to room temperature during 6 hours. The excess ethylene oxide and solvent were evaporated in vacuo and an oil was obtained. The oil can be crystallized from diisopropyl ether to give 3-(β-hydroxyethyl)-7-methoxy-1,2,4,5-tetrahydro-3H,3-benzazepine. m.p. 79°–80°.

Anal. Calc. for C$_{13}$H$_{19}$NO$_2$: C, 70.55; H, 8.65; N, 6.33. Found: C, 70.34; H, 8.33; N, 6.56.

The crude alcohol was dissolved in pyridine (25 ml.) and the solution was cooled to 10° C. Acetic anhydride (9 ml.) was added and the reaction was allowed to stand at room temperature for 16 hours. Evaporation of the pyridine and acetic anhydride in vacuo afforded a gum which was dissolved in water. The solution was basified with sodium carbonate solution and the precipitated oil was extracted into diethyl ether. Evaporation of the ether afforded an oil which was a mixture of the required ester and the alcohol. The oil was dissolved in benzene and acetyl chloride (1 ml.) was added. After 3 hours at room temerature the solvent was evaporated in vacuo and the residue was suspended in diethyl ether and treated with hydrogen chloride. The precipitated hydrochloride salt was filered and recrystallized from methylethylketone. m.p. 155°–157°. wt.=8 gm.

Anal. Calc. for C$_{15}$H$_{21}$NO$_3$·HCl: C, 60.07; H, 7.40; N, 4.67; Cl. 11.82. Found: C, 59.96; H, 7.31; N, 4.87; Cl, 11.82.

EXAMPLE 46

3-(β-Acetoxyethyl)-7-hydroxy-1,2,4,5-tetrahydro-3H,3-benzazepine

7-Hydroxy-1,2,4,5-tetrahydro-3H,3-benzazepine (13.98 gm., 0.0855 m) and triethylamine (17.9 gm., 0.18 m) were dissolved in dimethylformamide (60 ml.) and the solution was heated and stirred to 100°. 2-Chloroethylacetate (22 gm., 0.18 m) was added dropwise during 5 minutes. After 5 hours at 100° the reaction was cooled and diluted with ethyl acetate (300 ml.). The ethyl acetate extract was washed with water and dried over magnesium sulfate. Evaporation of the solvent in vacuo afforded an oil. The oil was extracted with hot diisopropyl ether and the resultant solution was cooled to −70° C. A gum precipitated and the supernatant solvent was decanted from it. The solution precipitated a small quantity (1.3 gm.) of the required ester. The solvent was evaporated in vacuo and the residue was combined with the gum from above and chromatogrammed on silica gel. Elution with benzene:methanol (9:1) afforded the required ester (4.7 gm.) as a gum. The combined products (1.3 gm. +4.7 gm.) were converted to the oxalate salt which was recrystallized from methanol:ether (2:1). m.p. 161°–163°.

Anal. Calc. for $C_{16}H_{21}NO_7$: C, 56.63; H, 6.24; N, 4.13. Found: C, 56.76; H, 6.25; N, 4.38.

EXAMPLE 47

3-(β-Acetoxypropyl)-7-hydroxy-1,2,4,5-tetrahydro-3H,3-benzazepine

7-Hydroxy-1,2,4,5-tetrahydro-3H,3-benzazepine (13 gm., 0.08 m) was suspended in methanol (200 ml.) at reflux. 1,2-Propylene oxide (5.55 gm., 0.096 m) was added dropwise during 10 minutes and the reaction was stirred and refluxed for further 15 minutes. An additional portion of 1,2-propylene oxide (1.66 gm., 0.0286 m) was added and the reaction was continued for 1 ½ hours. The excess reagent and methanol were evaporated in vacuo and the residue was crystallized from a mixture of methanol (35 ml.) and ethyl acetate (100 ml.) m.p. 162°–166°. The alcohol was recrystallized from ethyl acetate. m.p. 164°–166°.

Anal. Calc. for $C_{13}H_{19}NO_2$: C, 70.55; H, 8.65; N, 6.33. Found: C, 70.63; H, 8.63; N, 6.29.

Benzyl bromide (13.7 gm., 0.08 m) was added dropwise to a solution of 7-hydroxy-3-(β-hydroxypropyl)-1,2,4,5-tetrahydro-3H,3-benzazepine (14.7 gm., 0.0665 m) and potassium hydroxide (3.92 gm., 0.07 m) in absolute ethanol (80 ml.) at reflux, during 1.5 hours. The reaction was refluxed a further 1.5 hours. The precipitated potassium bromide was filtered and the filtrate was evaporated to dryness in vacuo. The residue was dissolved in ethyl acetate and water. The ethyl acetate extract was separated and dried over magnesium sulfate. Evaporation of the ethyl acetate afforded an oil. wt.=20.4 gm. The oil was chromatogrammed on silica gel and elution of the column with methanol:benzene (1:9) afforded the pure compound as an oil which solidified. m.p. 66°–70°. wt.=14 gm. The product was recrystallized from petroleum ether (40°–60°). m.p. 73°–75°.

Anal. Calc. for $C_{20}H_{25}NO_2$: C, 77.13; H, 8.09; N, 4.50 Found: C, 77.20; H, 7.95; N, 4.64.

7-Benzyloxy-3-(β-hydroxypropyl)-1,2,4,5-tetrahydro-3H,3-benzazepine (14 gm., 0.045 m) and triethylamine (5.05 gm. 0.05 m) were dissolved in benzene (100 ml.) and the solution was cooled to 10°. Acetyl chloride (3.92 gm., 0.05 m) was added dropwise to the stirred reaction during 15 minutes. After stirring the reaction for 2 hours at room temperature the benzene solution was filtered from the triethylamine hydrochloride. The benzene solution was washed with water, and sodium carbonate solution and then it was dried over magnesium sulfate. Evaporation of the benzene in vacuo afforded the crude ester. wt.=14 gm. The ester was hydrogenated in acetic acid solution (200 ml.) over 5% palladium charcoal (2 gm.) at 50 psi and at room temperature. After 8 hours the absorption of hydrogen had ceased and the catalyst was removed by filtration. The acetic acid was evaporated in vacuo and the residue was dissolved in chloroform. The chloroform solution was washed with sodium carbonate solution and water. Evaporation of the chloroform in vacuo afforded the title compound as an oil. wt.=10.2 gm. The oil was converted to the exalate salt and recrystallized from methanol. m.p. 195°–197°. wt. =6.5 gm.

Anal. Calc. for $C_{17}H_{23}NO_7$: C, 57.78; H, 6.56; N, 3.96 Found: C, 58.03; H, 6.51; N, 3.84.

EXAMPLE 48

(−)-2-Methyl-1,2,4,5-tetrahydro-3H,3-benzazepine

N-Toluene-p-sulfonyl-1-methyl-2-phenylethylamine

Dextro amphetamine (200 g) and triethylamine (164 g) were dissolved in 1500 ml. of benzene. A solution of p-toluene sulfonyl chloride (310g) in 500 ml. of benzene was added dropwise to the cooled solution during one hour. The reaction mixture was stirred for three hours at room temperature, then allowed to stand for approximately 16 hours (over night) at room temperature (approximately 20° C.). The salts were filtered off and the benzene solution was washed with dilute HCl, water and brine. Evaporation of the solvent afforded an oil.

d-N-toluene-p-sulfonyl-N-(1-methyl-2-phenyl)ethyl-glycine

The crude N-toluene-p-sulfonyl-1-methyl-2-phenylethylamine (240 g) was dissolved in 4 liters of acetone. Finely ground potassium carbonate (750g) was added and the suspension was brought to reflux. Ethylbromoacetate (208g) was added in six equal portions at 20 minute intervals. The reaction was refluxed approximately 16 hours (over night). The acetone solution was filtered and evaporated to an oil which was dissolved in 95% ethanol (4.8 liters) containing 10% aqueous NaOH (1 liter). The solution was refluxed for six hours and then permitted to stand at room temperature for three days. The ethanol was evaporated and the oily salt was dissolved in water (8 liters), washed with ether and acidified with concentrated HCl. The oily precipitate was extracted into ether, washed with sodium bicarbonate and the bicarbonate layer was acidified with concentrated HCl. The precipitated acid was isolated by ether extraction. Evaporation of the ether afforded a solid having a melting point of 114°–116° C. The solid was recrystallized from benzene/cyclohexane (250/300 ml) to give a melting point of 115°–118°. $[α]_{589}^{25}$ = +29.74°(C=2.04 in $CH_3OH$). d-4-Methyl-toluene-p-sulfonyl-1,2,4,5-tetrahydro-3H,3-benzazepin-1-one d-N-Toluene-p-sulfonyl-N-(1-methyl-2-phenyl)ethyl-glycine (200g), thionyl chloride (139g) and benzene (2 liters) were refluxed together for four hours and permitted to stand at room temperature for about 16 hours (over night). Evaporation of the solvents afforded a solid acid chloride, having a melting point at 97°–101°

C. IR showed a strong carbonyl absorption at 1800 cm$^{-1}$ (CO Cl). The acid chloride (0.575 M) was dissolved in methylene chloride (500 ml) and added dropwise to a suspension of aluminum chloride (306 g) and methylene chloride (2 liters) at (−) 70° C. during 1.5 hours. The reaction was stirred for 24 hours as it warmed to +10° C. The suspension was poured into ice (4 kg) water (4 liters), concentrated HCl (700 ml) and stirred for 1.5 hours. The methylene chloride layer was separated and the aqueous layer was washed twice with methylene chloride (500 ml) each. The methylene chloride layers were combined and washed with water, dilute NaOH solution, water and brine. The reaction product was dried over MgSO$_4$, the solvents evaporated and the solid recrystallized from 95% ethanol several times.$[\alpha]_{589}^{25} = +112.8°$ (C=0.023 in chloroform).

d-1-Hydroxy-4-methyl-3-toluene-p-sulfonyl-1,2,4,5-tetrahydro-3H,3-benzazepine d-4-Methyl-3-toluene-p-sulfonyl-1,2,4,5-tetrahydro-3H,3-benzazepin-1-one (155 g) was suspended in 95% ethanol (2 liters) and sodium borohydride (19 g) was added. The reaction was warmed to 70° C. during 30 minutes and then stirred while cooling for three hours. The ethanol solution and the suspended solid were poured cautiously with stirring into 6 liters of icewater/250 ml concentrated HCl. The gummy alcohol was extruded into chloroform. Evaporation of the chloroform afforded a solid. $[\alpha]_{589}^{25} = +26.08°$ (C=2.07 in CH$_3$OH).

d-2-Methyl-3-toluene-p-sulfonyl-1,2-dihydro-3H-3-benzazepine d-1-Hydroxy-4-methyl-3-toluene-p-sulfonyl-1,2,4,5-tetrahydro-3H,3-benzazepine was dissolved in benzene (1 liter) containing p-toluene sulfonic acid as a catalyst (1g). After refluxing in a Dean and Stark separator durinng which a total additional quantity of p-toluene sulfonic acid amounting to 3 g were added to the reaction, the benzene solution was washed with dilute NaOH to remove the catalyst, and the solvent was evaporated to give an oil. $[\alpha]_{589}^{25} = +51.4°$ (C=0.08 in methanol).

d-2-Methyl-3-toluene-p-sulfonyl-1,2,4,5-tetrahydro-3H,3-benzazepine d-2-Methyl-3-toluene-p-sulfonyl-1,2-dihydro-3H,3-benzazepine (117.5 g) was suspended in acetic acid (1 liter) along with 10 g of 5% Pd./C. The mixture was hydrogenated at room temperature in a 2 liter flask on a Parr apparatus at 45 psi. After 6.5 hours the flask was flushed with nitrogen and the solution was filtered through a pad of Celite. Some crystallization had occurred and the cake was washed with chloroform. Evaporation of the chloroform afforded a solid melting at 111°-113.0° C. After standing approximately 16 hours (over night) a solid crystallized from the acetic acid. The solid was filtered, melting point 112°-114° C. The acetic acid was removed by evaporation to a volume of 200 ml and the precipitated solid was filtered, melting point 112°-114° C. The filtrate was evaporated and the solids residue was washed with isopropyl ether to give a solid, melting point 111°-113.5° C. $[\alpha]_{589}^{25} = +38.0°$ (C=2.03 in chloroform).

(−)-2-Methyl-1,2,4,5-tetrahydro-3H,3-benzazepine

A sodium naphthalene solution in 1,2-dimethoxy ethane (3 L) was prepared from sodium (39 g) and naphthalene (236 g) at 25°-35° C. during 2 hours. Solid d-2-methyl-3-toluene-p-sulfonyl-1,2,4,5-tetrahydro-3H,3-benzazepinne (90 g) was added during 20 minutes at 22°-26° C. with a cooling bath in place. The reaction was stirred for 2.5 hours at room temperature (about 20° C.). The reaction mixture was decomposed by adding water (50 ml) at 15°-20° C. and evaporating the solvent. The residue was dissolved in ether/water and the ether layer was separated. The ether was washed with dilute HCl and the acid layer was separated. Aqueous sodium hydroxide was added and the amine isolated in ether afforded an oil. The oil was converted to the hydrochloride which was gummy. Trituration with hot acetone (200 ml) afforded a brown solid which later turned blue, melting point 184°-187° C. Ether was added to the acetone and further 8.4 g was obtained, melting point 178°-182° C. The dark green filtrates were evaporated and the residue dissolved in water. Basification with aqueous NaOH and extraction with ether afforded an oil. The oil was converted to the hydrochloride in ether and the gummy salt was treated with warm acetone and the resulting solid was filtered, melting point less than 140° C. The solid was dissolved in acetone (50 ml)/isopropanol (17.5 ml) at reflux and cooled in a refrigerator at about 4° C. The first crop of crystals was filtered, melting point 178°-182° C. The filtrate was evaporated and the gummy residue was triturated with acetone and the solid filtered, melting point 120°-130° C. The salts so prepared were combined and made basic with NaOH and the free amine was isolated in ether. The oil was distilled to give a colorless amine which afforded a solid hydrochloride from ether. The salt was dissolved in hot isopropanol (125 ml), filtered and diluted with ether (125 ml). Immediate crystallization began and the suspension was stirred for 16 hours at room temperature. The salt was filtered to give a solid melting at 183°-187° C. $[\alpha]_{578}^{25} = -32.39°$ (C=1.05 in CH$_3$OH).

EXAMPLE 49

(+)-2-Methyl-1,2,4,5-tetrahydro-3H,3-benzazepine hydrochloride (766-476)

The procedure of Example 49 was repeated except that l-amphetamine was used as the starting material to give 29.5 g of solid, a 20 g. portion of which was recrystallized from 50 ml. butanol to give 14. g. of product, m. 187°-191° C.

|  | C | H | N | Cl |
|---|---|---|---|---|
| Calcd. | 66.82 | 8.15 | 7.08 | 17.93 |
| Found | 66.82 | 8.16 | 7.08 | 17.87 |

EXAMPLE 50

(+)-2,3-Dimethyl-1,2,4,5-tetrahydro-3H,3-benzazepine hydrochloride (766-438)

(−)-2-Methyl-1,2,4,5-tetrahydro-3H,3-benzazepine base (from 10 g. of the HCl salt) was refluxed with 28 ml. formic acid and 24 ml. formalin for six hours, concentrated to dryness and the residue treated with aqueous NaOH and ether. The ether residue was converted to the hydrochloride in ether and the salt recrystallized from a mixture of 140 ml. isopropanol and 15 ml methanol to give 5.5 g. product, m. 260°-270° (dec).

|  | C | H | N | Cl |
|---|---|---|---|---|
| Calcd. | 68.08 | 8.57 | 6.62 | 16.75 |
| Found | 68.05 | 8.39 | 6.56 | 16.76 |

$[\alpha]_{578}^{25} = +0.33°$ (C=1.81 in methanol)

EXAMPLE 51

(−)
8-Methoxy-2-methyl-1,2,4,5-tetrahydro-3H,3-benzazepine (786-772)

Racemic 8-methoxy-2-methyl-1,2,4,5-tetrahydro3H,3-benzazepine (44 g, 0.22 M) was dissolved in absolute methanol (250 ml) and added to a solution of D (+) tartaric acid (34.5 g, 0.23 M) in methanol (400 ml). The resulting solution was filtered and allowed to stand at room temperature for three days. The methanol was filtered from the dense crystalline material. Wt=24 g. A second crop was obtained by concentrating the filtrate to 300 ml and standing for 24 hr. Wt=7.3 g. The combined solids were recrystallized from methanol (500 ml) and after 24 hr the solid precipitate was filtered. Wt=21.6 g. This salt was again recrystallized from methanol (350 ml) and after 24 hr the precipitate was filtered: Wt=16.3 g. $[\alpha]_{578}^{25°} = -4.8°$; (C=1.08 in H$_2$O)

Concentration of the filtrates from the second and third crystallizations afforded more materials which were combined and recrystallized twice from methanol to give more of the required salt. Wt=3.8 g. $[\alpha]_{578}^{25°} = -5.4°$; (C=1.00 in H$_2$O). The combined salts were dissolved in water and basified with 10% sodium hydroxide solution. The amine was isolated by extraction into benzene. Evaporation of the benzene afforded the amine. Wt=10.5 g, yield=25%. A sample of the hydrochloride had $[\alpha]_{578}^{25°} = (-) 26.8°$; (C=0.89 in H$_2$O).

|  | C | H | N | Cl |
|---|---|---|---|---|
| Theory % : | 63.29 | 7.97 | 6.15 | 15.57 |
| Found % : | 62.72 | 7.62 | 6.05 | 15.47 |
|  | 63.24 | 7.84 | 5.98 | 15.51 |
|  | 63.07 | 7.65 | 5.98 |  |

EXAMPLE 52

(+)-8-Methoxy-2-methyl-1,2,4,5-tetrahydro-3H,3-benzazepine(−)-bitartrate

The procedure of Example 52 was repeated except that D(−) tartaric acid was used instead of D(+) tartaric acid. A sample of the D(−) tartrate salt was dried at 80° for six hours and submitted for analysis.

|  | C | H | N |
|---|---|---|---|
| Calcd. | 56.30 | 6.79 | 4.10 |
| Found | 56.19 | 7.17 | 4.03 |

Optical Rotation $[\alpha]_{578}^{25} = +5.36°$ (C=1.01 in H$_2$O)

EXAMPLE 53

(+)-8-Methoxy-2-methyl-1,2,4,5-tetrahydro-3H,3-benzazepine hydrochloride (786-776)

The D(−) tartrate salt (10 g) was dissolved in water, the solution made alkaline and extracted with CHCl$_3$. The CHCl$_3$ extract was washed with water, dried and concentrated to dryness. The residue was dissolved in isopropanol treated with HCl gas. The solid was filtered and dried under vacuum at 100° to give 7 g product, m. 243°-244°, $[\alpha]_{578}^{25} = +27.11$. (C=1.0 in H$_2$O)

|  | Calcd | Found |
|---|---|---|
| C | 63.29 | 62.99 |
| H | 7.97 | 7.73 |
| Cl | 15.57 | 15.34 |
| N | 6.15 | 5.89 |

EXAMPLE 54

(−)-2,3-Dimethyl-1,2,4,5-tetrahydro-3H,3-benzazepine hydrochloride (766-477)

(+) -2-Methyl-1,2,4,5-tetrahydro-3H,3-benzazepine (10 g.) was refluxed six hours with 35 ml. formic acid and 29 ml. formalin. The mixture was concentrated to dryness and the residue treated with 10% NaOH and ether. The ether was separated, washed with water and brine, dried and concentrated. The residue was dissolved in ether and treated with HCl gas to give a solid which was recrystallized from a mixture of 100 ml. isopropanol and 20 ml. methanol to give 8.9 g., m. 268°-272°.

|  | C | H | N | Cl |
|---|---|---|---|---|
| Calcd. | 68.07 | 8.57 | 6.62 | 16.74 |
| Found | 68.33 | 8.58 | 6.64 | 16.53 |

$[\alpha]_{589}^{25} = -0.71$ (C=0.98 in CH$_3$OH)

EXAMPLE 55

(−)-3-(3,3-Dimethylallyl)-8-hydroxy-2-methyl-1,2,4,5-tetrahydro-3H,3-benzazepine hydrochloride (795-232)

Step 1: (−)-8-hydroxy-2-methyl-1,2,4,5-tetrahydro-3H,3-benzazepine was prepared from (−)-8-methoxy-2-methyl-1,2,4,5-tetrahydro-3H,3-benzazepine refluxed with 48% HBr in accordance with the procedure described in Example 2.

Step 2: (−)-8-Hydroxy-2-methyl-1,2,4,5-tetrahydro-3H,3-benzazepine (27.7 g.) and 25 g. triethylamine were dissolved in 200 ml. dimethylformamide at 50°-60°. 1-Bromo-3-methyl-2-butene (18.6 g.) was added dropwise over 15 minutes and the reaction kept at 50°-60° for 4 hours, cooled, and poured into one liter of water. The amine was extracted with ethyl acetate, the extract washed with water and brine, dried and concentrated to an oil which was chromatographed on silica. The product was converted to the hydrochloride in methanol, the solvent evaporated and the residue recrystallized from 80 ml. isopropanol to give 11.2 g. product, m. 190-193.

|  | C | H | N | Cl |
|---|---|---|---|---|
| Calcd. | 68.19 | 8.58 | 4.97 | 12.58 |
| Found | 68.18 | 8.74 | 4.72 | 12.70 |

$[\alpha]_{578}^{25} = -4.7°$ (C=1.03 in H$_2$O)

EXAMPLE 56

(+)-3-(3,3-Dimethylallyl)-8-hydroxy-2-methyl-1,2,4,5-tetrahydro-3H,3-benzazepine hydrochloride (795-299)

Step 1: Step 1 of Example 56 was repeated except that (+)-8-methoxy-2-methyl-1,2,4,5-tetrahydro-3H,3-benzazepine was refluxed with 48% HBr to give (+)-8-hydroxy-2-methyl-1,2,4,5-tetrahydro-3H,3-benzazepine.

Step 2: (+)-8-Hydroxy-2-methyl-1,2,4,5-3H,3-benzazepine hydrobromide (4.5 g.) was dissolved in 40 ml. dimethylformamide, 3.9 g. triethylamine added and the reaction warmed to 40°. 1-Bromo-3-methyl-2-butene (2.88 g.) was added over ten minutes. After four hours the reaction was poured into 200 ml. water and extracted with ethyl acetate. The extract was dried and concentrated to give an oil. The oil, combined with the product from another reaction using 25 g. of the hydrobromide was chromatographed on silica and the product dissolved in methanol, treated with HCl gas, the solution concentrated and the residue recrystallized from 85 ml. isopropanol to give 10.8 g. product, m. 191–194.

|        | C     | H    | N    | Cl    |
|--------|-------|------|------|-------|
| Calcd. | 68.19 | 8.58 | 4.97 | 12.58 |
| Found  | 68.52 | 8.50 | 4.67 | 12.62 |

$[\alpha]_{578}^{25} = +4.7$ (C=0.99 in $H_2O$)

EXAMPLE 57

(+)-8Hydroxy-2,3-dimethyl-1,2,4,5tetrahydro-3H,3-benzazepine hydrochloride 893-771)

(+)-8-Methoxy-2-methyl-1.2,4,5-tetrahydro-3H,3-benzazepine (20 g.) was refluxed with 48 ml. formalin and 56 ml. formic acid for six hours and concentrated under vacuum. The benzene extract was washed with water, dried and concentrated. The residue was dissolved in ether and treated with dry HCl. The resultant solid (+)-8-methoxy-2,3-dimethyl-1,2,4,5-tetrahydro-3H,3-benzazepine hydrochloride was recrystallized by dissolving in butanol and adding tetrahydrofuran and ether to give 7.5 g., m. 200–202. (+)-8-Methoxy-2,3-dimethyl-1,2,4,5-tetrahydro-3H,3-benzazepine hydrochloride (10 g.) was dissolved in 60 ml. 48% HBr, refluxed for three hours, and evaporated to dryness. The residue was dissolved in water, made alkaline with $Na_2CO_3$, and extracted with ethyl acetate. The extract was dried, concentrated to dryness and the residue dissolved in isopropanol and treated with dry HCl to give 7 g. product, m. 242–244.

|        | C     | H    | N    | Cl    |
|--------|-------|------|------|-------|
| Calcd. | 63.29 | 7.97 | 6.15 | 15.57 |
| Found  | 63.10 | 8.30 | 5.89 | 15.37 |

$[\alpha]_{578}^{25} = +12.4°$ (C=0.99 in $H_2O$)

EXAMPLE 58

3-(P-Hydroxyphenethyl-8-methoxy-2-methyl-1,2,4,5-tetrahydro-3H,3-benzazepine hydrochloride (815-011)

3-(P-Acetoxyphenylacetyl)-8-methoxy-2-methyl-1,2,4,5-tetrahydro-3H,3-benzazepine To 8.6 g of 8-methoxy-2-methyl-1,2,4,5-tetrahydro-3H,3-benzazepine (example 32) in 50 ml benzene was added 6.3 of triethylamine. To this was added dropwise with cooling a solution of p-acetoxy-phenylacetyl chloride (prepared from 8.7 g p-acetoxy-phenylacetic acid and thionyl chloride) in 50 ml benzene. The mixture was stirred 2 hours at room temperature, washed with water, dilute HCl, water, dilute $Na_2CO_3$, and water, then dried and concentrated to give 13.7 g of a thick oil.

3-(P-Hydroxyphenethyl-8-methoxy-2-methyl-1,2,4,5-tetrahydro-3H,3-benzazepine hydrochloride.

To 3.5 g. $LiAlH_4$ in 200 ml dry tetrahydrofuran (THF) was added dropwise over a 20-minute period 13.7 g of 3-(P-acetoxphenylacetyl)-8-methoxy-2-methyl-1,2,4,5-tetrahydro-3H,3-benzazepine in 50 ml dry THF. The mixture was stirred 22 hours at room temperature and treated with aqueous ammonium tartrate solution. The THF was separated and the aqueous layer extracted twice with chloroform. The THF and chloroform, washed with water, dried and concentrated on the rotovap to give 11.7 g residue. The residue was dissolved in 100 ml methanol, filtered through celite and treated with dry HCl to give 10 g of the HCl sale which was recrystallized from 270 ml 75% ethanol to give 7.7 g product, m. 273–276.

|       | C     | H    | N    | Cl    |
|-------|-------|------|------|-------|
| Calc. | 69.05 | 7.53 | 4.03 | 10.19 |
| Found | 68.74 | 7.24 | 3.97 | 10.12 |

EXAMPLE 59

3-(o-Methylphenethyl)-8-methoxy-2-methyl-1,2,4,5-tetrahydro-3H,3-benzazepine hydrochloride (814-823)

3-(o-Methylphenylacetyl)-8-methoxy-2-methyl-1,2,4,5-tetrahydro-3H,3-benzazepine

To a mixture of 5 g 8methoxy-2-methyl-1,2,4,5-tetrahydro-3H,3-benzazepine (example 32) and 3.53 g triethyl-amine in 100 ml benzene was added o-methylphenyl-acetyl chloride (prepared from 4.3 g o-methyl-phenyl-acetic acid and thionyl chloride) in 25 ml benzene. The mixture was stirred 1 hour, left overnight at room temperature, filtered, washed with dilute HCl and saturated $Na_2CO_3$, then dried and concentrated to dryness.

3-(o-Methylphenethyl)-8-methoxy-2-methyl-1,2,4,5-tetrahydro-3H,3-benzazepine hydrochloride To a suspension of 2.05 g $LiALH_4$ in 90 ml tetrahydrofuran (THF) was added dripwise a solution of 8.4 g of 3-(o-methylphenylacetyl)-8-methoxy-2-methyl-1,2,4,5-tetrahydro-3H,3-benzazepine in 75 ml THF. The mixture was refluxed 2 hours, then added 2 ml water. 2 ml 15% NaOH and 8.1 ml water. The mixture was filtered and the filtrate dried and concentrated to dryness. The residue was dissolved in ether and treated with HCl gas. The precipitated oil was separated, dissolved in 5 m. methanol and 20 ml ether was added to give 3.7 g product, m. 191-3.

|       | C     | H    | N    | Cl   | $H_2O$ |
|-------|-------|------|------|------|--------|
| Calc. | 70.76 | 8.36 | 3.84 | 9.90 |        |
| Found | 70.68 | 8.62 | 3.68 | 9.85 | 0.59   |

EXAMPLE 60

3-Furfuryl-7-hydroxy-1,2,4,5-tetrahydro-3H,3-benzazepine hydrochloride (811-053)

3-(2-Furancarbonyl)-7-(2-furancarbonyloxy)-1,2,4,5-tetrahydro-3H,3-benzazepine

7-Hydroxy-1,2,4,5-tetrahydro-3H,3-benzazepine hydrobromide (example 2) (11.9 g.) was dissolved in 40 ml. dimethylformamide with 4.5 g. triethylamine. Furoyl chloride (12.5 g.) was added dropwise with cooling. Another equivalent of triethylamine and furoyl chloride was added and the mixture stirred ½ hour. Water (100 ml.) was added, the mixture extracted with ethyl acetate, and the ethyl acetate extract washed with dilute HCl, NaHCO3 solution, water, and saturated NaCl. The solution was dried and concentrated to give 16.8 g. product.

3-Furfuryl-7-hydroxy-1,2,4,5-tetrahydro-3H,3-benzazepine hydrochloride

The product from the previous step (16.8 g.) was dissolved in 158 ml. tetrahydrofuran (THF) and added dropwise to 4.0 g. LiAlH4 in 400 ml. THF. The mixture was stirred 18 hours at room temperature, then added 39 ml. ethyl acetate (dropwise), 595 ml. saturated ammonium tartrate and stirred for 1 hour. The THF layer was separated and the aqueous fraction extracted with THF and then with CHCl3. The THF was concentrated and the residue dissolved in water and extracted with CHCl3. The CHCl3 extract was concentrated, the residue dissolved in a minimum of THF and acidified with HCl gas, then diluted with 2 volumes of ether. The solid was filtered and recrystallized twice from propanol to give 7.4 g. product, m. 224–226.

|   | Calcd | Found |
|---|-------|-------|
| C | 64.63 | 64.44 |
| H | 6.15  | 6.25  |
| N | 5.02  | 5.01  |
| Cl| 12.72 | 12.67 |

EXAMPLE 61

3-Methoxy-3-(p-methoxyphenethyl)-2-methyl-1,2,4,5-tetrahydro-3H,3-benzazepine hydrochloride (814-807)

8Methoxy-3-(p-methoxyphenylacetyl)-2-methyl-1,2,4,5-tetrahydro-3H,3-benzazepine

8-Methoxy-2-methyl-1,2,4,5-tetrahydro-3H,3-benzazepine (example 32) (5 g.) was dissolved in 28 ml. tetrahydrofuran (THF) and mixed with 6.3 g. dicyclohexylcarbodiimide in 24 ml. THF. The mixture was cooled to 20°–30° while adding 4.7 g. 4-methoxyphenylacetic acid in 28 ml. THF. Acetic acid (0.3 ml.) was added and the mixture concentrated to dryness and purified by chromatography to give 4 g. product.

8-Methoxy-3-(p-methoxyphenethyl-2-methyl-1,2,4,5-tetrahydro-3H,3-benzazepine hydrochloride The product from the previous step (4 g.) was dissolved in 34 ml. THF and added dropwise to 0.9 g. LiAlH4 in 40 ml. THF. The mixture was refluxed 24 hours, then added 0.9 ml. water, 0.9 ml. 15% NaOH, 2.7 ml. water, and filtered, dried and concentrated. The residue was dissolved in methanol, acidified with HCl gas, and ether added until precipitation just started. The solid was filtered and washed to give 1.0 g., m. 198–199. Addition of more ether gave a second crop of 1.3 g., m. 197.5–8.5.

|    | Calcd | Found |
|----|-------|-------|
| C  | 69.69 | 69.57 |
| H  | 7.80  | 7.70  |
| N  | 3.87  | 3.86  |
| Cl | 9.79  | 9.83  |

EXAMPLE 62

(+)-8-Methoxy-2,3-dimethyl-1,2,4,5-tetrahydro-3H,3-benzazepine hydrochloride (793-770)

This compound was prepared as an intermediate in example 58 from (+)-8-methoxy-2-methyl-1,2,4,5-tetrahydro-3H,3-benzazepine. $[\alpha_{578}^{25}] = +11.90$ (C=0.99 in H$_2$O)

|    | Calcd (adjusted for 1.46% H$_2$O) | Found |
|----|-----------------------------------|-------|
| C  | 63.62 | 63.40 |
| H  | 8.38  | 8.29  |
| N  | 5.70  | 5.28  |
| Cl | 14.49 | 14.43 |

EXAMPLE 63

(−)-8-Methoxy-2,3-dimethyl-1,2,4,5-tetrahydro-3H,3-benzazepine hydrochloride (795-234)

This compound was prepared the same way as the (+) isomer except that the starting material was (−)-8-methoxy-2-methyl-1,2,4,5-tetrahydro-3H,3-benzazepine. Yield of product was 6.65 g. from 9 g. of starting material. The product m. 202°–204°. $[\alpha_{578}^{25}] = -11.05$ (C=1.08 in H$_2$O)

|    | Calcd | Found |
|----|-------|-------|
| C  | 64.59 | 64.49 |
| H  | 8.34  | 7.72  |
| N  | 5.79  | 5.44  |
| Cl | 14.66 | 14.72 |

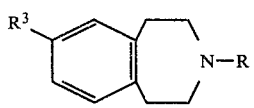

| R³    | R              | R¹ | Additional Examples |
|-------|----------------|----|---------------------|
| CH₃O  | CH₃—CH=CH—CH₂— |    | 3-(3-Methylallyl)-7-methoxy-1,2,4,5-tetrahydro-3H,3-benzazepine |
| HO    | CH₃—CH=CH—CH₂— |    | 7-Hydroxy-3-(3-methylallyl)-1,2,4,5-tetrahydro-3H,3-benzazepine |

-continued

| R³ | R | Name |
|---|---|---|
| CH₃O | phenyl-CH₂CH₂CH₂— | 7-Methoxy-3-(3-phenylpropyl)-1,2,4,5-tetrahydro-3H,3-benzazepine |
| HO | phenyl-CH₂CH₂CH₂— | 7-Hydroxy-3-(3-phenylpropyl)-1,2,4,5-tetrahydro-3H,3-benzazepine |
| CH₃O | CH₂=C(CH₃)—CH₂— | 7-Methoxy-3-(2-methylallyl)-1,2,4,5-tetrahydro-3H,3-benzazepine |
| CH₃O | 4-pyridyl-CH₂—CH₂— | 7-Methoxy-3-[2-(4-pyridyl)-ethyl]-1,2,4,5-tetrahydro-3H,3-benzazepine |
| HO | 4-pyridyl-CH₂—CH₂— | 7-Hydroxy-3-[2-(4-pyridyl)-ethyl]-1,2,4,5-tetrahydro-3H,3-benzazepine |

Structure: R³-substituted benzazepine with 2-CH₃ group, N—R

| R³ | R | R¹ | Additional Examples |
|---|---|---|---|
| CH₃O | (CH₃)₂C=CH—CH₂— | | 3-(3,3-Dimethylallyl)-8-methoxy-2-methyl-1,2,4,5-tetrahydro-3H,3-benzazepine |
| CH₃O | (CH₃)₂C=CH—CH₂— | | (+)-3-(3,3-Dimethylallyl)-8-methoxy-2-methyl-1,2,4,5-tetrahydro-3H,3-benzazepine |
| CH₃O | (CH₃)₂C=CH—CH₂— | | (−)-3-(3,3-Dimethylallyl)-8-methoxy-2-methyl-1,2,4,5-tetrahydro-3H,3-benzazepine |
| HO | (CH₃)₂C=CH—CH₂— | | 3-(3,3-Dimethylallyl)-8-hydroxy-2-methyl-1,2,4,5-tetrahydro-3H,3-benzazepine |
| HO | (CH₃)₂C=CH—CH₂— | | (+)-3-(3,3-Dimethylallyl)-8-hydroxy-2-methyl-1,2,4,5-tetrahydro-3H,3-benzazepine |
| HO | (CH₃)₂C=CH—CH₂— | | (−)-3-(3,3-Dimethylallyl)-8-hydroxy-2-methyl-1,2,4,5-tetrahydro-3H,3-benzazepine |
| CH₃O | cyclopropyl-CH₂— | | 3-Cyclopropylmethyl-8-methoxy-2-methyl-1,2,4,5-tetrahydro-3H,3-benzazepine |
| HO | cyclopropyl-CH₂— | | 3-Cyclopropylmethyl-8-hydroxy-2-methyl-1,2,4,5-tetrahydro-3H,3-benzazepine |
| CH₃O | cyclobutyl-CH₂— | | 3-Cyclobutylmethyl-8-methoxy-2-methyl-1,2,4,5-tetrahydro-3H,3-benzazepine |
| HO | cyclobutyl-CH₂— | | 3-Cyclobutylmethyl-8-hydroxy-2-methyl-1,2,4,5-tetrahydro-3H,3-benzazepine |
| CH₃O | CH₂=CH—CH₂— | | 3-Allyl-8-methoxy-2-methyl-1,2,4,5-tetrahydro-3H,3-benzazepine |
| HO | CH₂=CH—CH₂— | | 3-Allyl-8-hydroxy-2-methyl-1,2,4,5-tetrahydro-3H,3-benzazepine |
| CH₃O | CH₂=C(CH₃)—CH₂— | | 8-Methoxy-2-methyl-3-(2-methylallyl)-1,2,4,5-tetrahydro-3H,3-benzazepine |
| HO | CH₂=C(CH₃)—CH₂— | | 8-Hydroxy-2-methyl-3-(2-methylallyl)-1,2,4,5-tetrahydro-3H,3-benzazepine |
| CH₃O | phenyl-CH₂CH₂— | | 8-Methoxy-2-methyl-3-phenethyl-1,2,4,5-tetrahydro-3H,3-benzazepine |
| HO | phenyl-CH₂CH₂— | | 8-Hydroxy-2-methyl-3-phenethyl-1,2,4,5-tetrahydro-3H,3-benzazepine |
| CH₃O | phenyl-CH=CH—CH₂— | | 8-Methoxy-2-methyl-3-(3-phenylallyl)-1,2,4,5-tetrahydro-3H,3-benzazepine |

-continued

| R³ | R | R¹ | Additional Examples |
|---|---|---|---|
| HO | (phenyl)-CH=CH-CH₂- | | 8-Hydroxy-2-methyl-3-(3-phenylallyl)-1,2,4,5-tetrahydro-3H,3-benzazepine |
| CH₃O | H | | 8-Methoxy-2-methyl-1,2,4,5-tetrahydro-3H,3-benzazepine |
| HO | H | | 8-Hydroxy-2-methyl-1,2,4,5-tetrahydro-3H,3-benzazepine |
| H | H | | 2-Methyl-1,2,4,5-tetrahydro-3H,3-benzazepine |

Structure: R³-substituted benzazepine with R¹ at position 2 and N—R

| R³ | R | R¹ | Additional Examples |
|---|---|---|---|
| CH₃OCH₂O | (CH₃)₂C=CH—CH₂ | H— | O-Methoxymethyl-3-(3,3-dimethylallyl)-7-hydroxy-1,2,4,5-tetrahydro-3H,3-benzazepine |
| CH₃OCH₂O | (CH₃)₂C=CH—CH₂ | CH₃— | O-Methoxymethyl-3-(3,3-dimethylallyl)-3-hydroxy-2-methyl-1,2,4,5-tetrahydro-3H,3-benzazepine |
| (nicotinoyl)-CO-O | (CH₃)₂C=CH—CH₂ | H— | 3-(3,3-Dimethylallyl)-7-nicotinoyloxy-1,2,4,5-tetrahydro-3H,3-benzazepine |
| (nicotinoyl)-CO-O | (CH₃)₂C=CH—CH₂— | CH₃ | 3-(3,3-Dimethylallyl)-2-methyl-8-nicotinoyloxy-1,2,4,5-tetrahydro-3H,3-benzazepine |
| CH₃O | (CH₃)₂C=CH—CH₂— | phenyl | 3-(3,3-Dimethylallyl)-8-methoxy-2-phenyl-1,2,4,5-tetrahydro-3H,3-benzazepine |
| HO | (CH₃)₂C=CH—CH₂— | phenyl | 3-(3,3-Dimethylallyl)-8-hydroxy-2-phenyl-1,2,4,5-tetrahydro-3H,3-benzazepine |
| CH₃O | (CH₃)₂C=CH—CH₂— | benzyl (—CH₂—phenyl) | 2-Benzyl-3-(3,3-dimethylallyl)-8-methoxy-1,2,4,5-tetrahydro-3H,3-benzazepine |
| HO | (CH₃)₂C=CH—CH₂— | benzyl (—CH₂—phenyl) | 2-Benzyl-3-(3,3-dimethylallyl)-8-hydroxy-1,2,4,5-tetrahydro-3H,3-benzazepine |
| CH₃O | (CH₃)₂C=CH—CH₂— | C₂H₅— | 3-(3,3-Dimethylallyl)-2-ethyl-8-methoxy-1,2,4,5-tetrahydro-3H,3-benzazepine |
| HO | (CH₃)₂C=CH—CH₂— | C₂H₅— | 3-(3,3-Dimethylallyl)-2-ethyl-8-hydroxy-1,2,4,5-tetrahydro-3H,3-benzazepine |
| CH₃O | (phenyl)-CH=CH—CH₂— | | 8-Methoxy-1-methyl-3-(3-phenylallyl)-1,2,4,5-tetrahydroxy-3H,3-benzazepine |
| HO | (phenyl)-CH=CH—CH₂— | | 8-Hydroxy-1-methyl-3-(3-phenylallyl)-1,2,4,5-tetrahydro-3H,3-benzazepine |

Structure: benzazepine with R³ at position 6 and R¹ at position 1, N—R

| R³ | R | R¹ | Additional Examples |
|---|---|---|---|
| CH₃O | (CH₃)₂C=CH—CH₂— | H | 3-(3,3-Dimethylallyl)-6-methoxy-1,2,4,5-tetrahydro-3H,3-benzazepine |
| HO | (CH₃)₂C=CH—CH₂— | H | 3-(3,3-Dimethylallyl)-6-hydroxy-1,2,4,5-tetrahydro-3H,3-benzazepine |

-continued

| | | | |
|---|---|---|---|
| CH₃O | (CH₃)₂C=CH—CH₂— | CH₃ | 3-(3,3-Dimethylallyl)-6-methoxy-2-methyl-1,2,4,5-tetrahydro-3H,3-benzazepine |
| HO | (CH₃)₂C=CH—CH₂— | CH₃ | 3-(3,3-Dimethylallyl)-6-hydroxy-2-methyl-1,2,4,5-tetrahydro-3H,3-benzazepine |

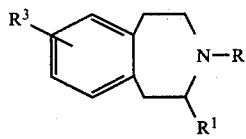

| R | R¹ | R³ |
|---|---|---|
| CH₂CH₂N⟨piperazine⟩N—Ph | H | HO |
| CH₃-CH(—CH₂N⟨piperazine⟩N—Ph) | H | HO |
| CH₂CH₂N⟨piperidine⟩ | H | HO |
| CH₃-CH(—CH₂N⟨piperidine⟩) | H | HO |
| CH₃-CH(—CH₂N⟨piperidine⟩-Ph) | H | HO |
| CH₂CH₂N⟨piperidine⟩-Ph | H | HO |
| CH₂CH₂N⟨piperidine with Ph, OH⟩ | H | HO |
| CH₃-CH(—CH₂N⟨piperidine with Ph, OH⟩) | H | HO |
| CH₂CH₂N⟨morpholine⟩O | H | HO |
| CH₃-CH(—CH₂N⟨morpholine⟩O) | H | HO |
| CH₂CH₂N⟨piperazine⟩N—Ph | H | CH₃O |
| CH₃-CH(—CH₂N⟨piperazine⟩N—Ph) | H | CH₃O |
| CH₂CH₂N⟨piperidine⟩ | H | CH₃O |

-continued

| | | |
|---|---|---|
| CH₃-CH-CH₂N⟨piperidine⟩ | H | CH₃O |
| CH₃-CH-CH₂N⟨piperidine-Ph⟩ | H | CH₃O |
| CH₂CH₂N⟨piperidine-Ph⟩ | H | CH₃O |
| CH₂CH₂N⟨piperidine(Ph)(OH)⟩ | H | CH₃O |
| CH₃-CHCH₂N⟨piperidine(Ph)(OH)⟩ | H | CH₃O |
| CH₃-CHCH₂N⟨piperidine(Ph)(OAc)⟩ | H | CH₃O |
| CH₂CH₂N⟨piperidine(Ph)(OAc)⟩ | H | CH₃O |
| CH₃-CHCH₂N⟨piperidine(Ph)(OC(=O)Et)⟩ | H | CH₃O |
| CH₂CH₂N⟨piperidine(Ph)(OC(=O)Et)⟩ | H | CH₃O |
| CH₂CH₂N(Me)₂ | H | CH₃O |
| CH₃-CHCH₂N(Me)₂ | H | CH₃O |
| CH₂CH₂N(Et)₂ | H | CH₃O |
| CH₃-CHCH₂N(Et)₂ | H | CH₃O |
| CH₂CH₂N⟨morpholine⟩ | H | CH₃O |
| CH₃-CHCH₂N⟨morpholine⟩ | H | CH₃O |
| CH₂CH₂N⟨piperazine-N-Ph⟩ | CH₃ | HO |
| CH₂CH₂N⟨piperazine-N-Ph⟩ | CH₃ | CH₃O |
| CH₂CH₂N⟨piperidine(Ph)(OAc)⟩ | CH₃ | HO |

-continued
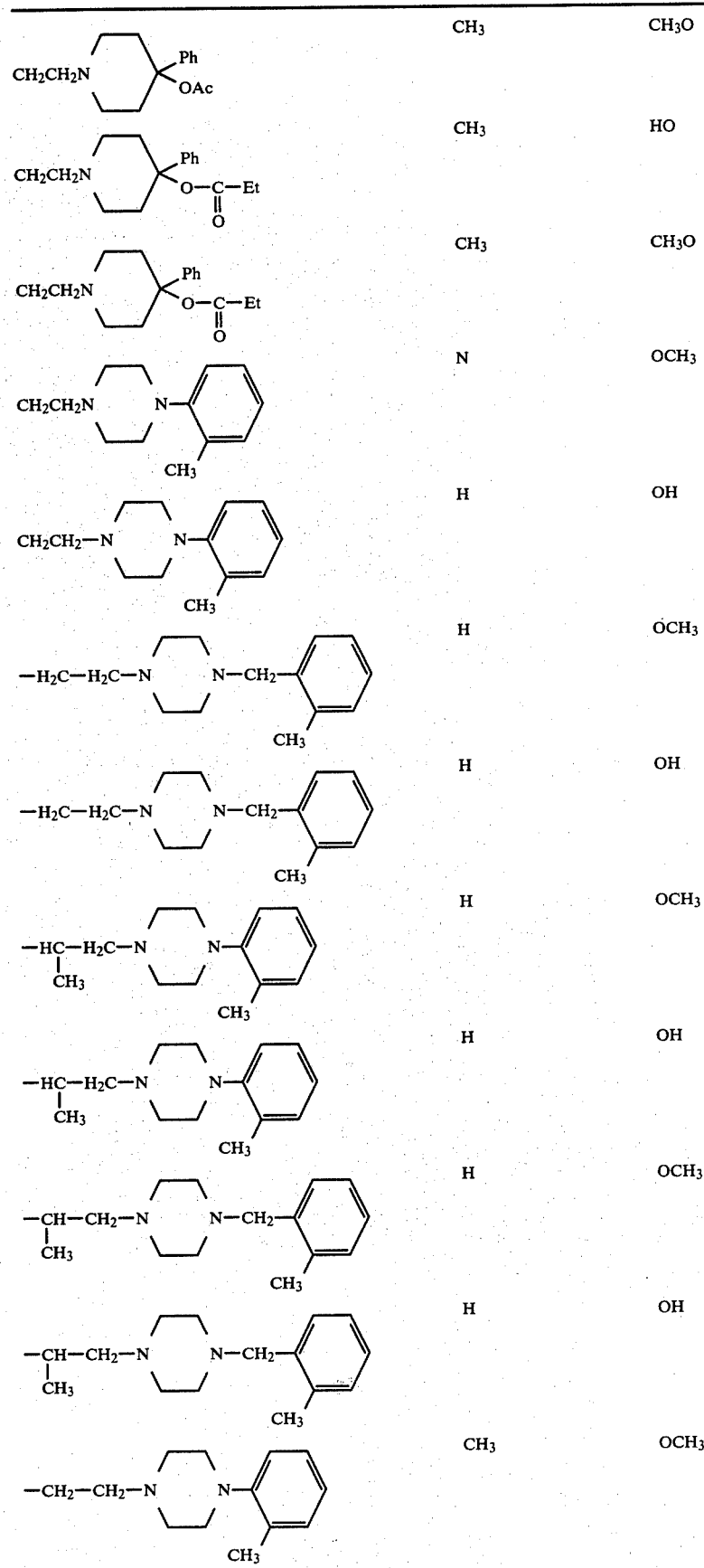
| | | |
|---|---|---|
| | CH₃ | CH₃O |
| | CH₃ | HO |
| | CH₃ | CH₃O |
| | N | OCH₃ |
| | H | OH |
| | H | OCH₃ |
| | H | OH |
| | H | OCH₃ |
| | H | OH |
| | H | OCH₃ |
| | H | OH |
| | CH₃ | OCH₃ |

-continued

| Group 1 | Group 2 | Group 3 |
|---|---|---|
| −CH₂−CH₂−N(piperazinyl)−(2-methylphenyl) | CH₃ | OH |
| −CH₂−CH₂−N(piperazinyl)−N−CH₂−phenyl | H | OCH₃ |
| −CH₂−CH₂−N(piperazinyl)−N−CH₂−phenyl | H | OH |
| −CH₂−CH₂−N(phthalimido) | H | OCH₃ |
| −CH₂−CH₂−N(phthalimido) | H | OH |
| −CH₂−CH₂−N(CH₂−phenyl−CH₂) (isoindoline) | H | OCH₃ |
| −CH₂−CH₂−N(CH₂−phenyl−CH₂) (isoindoline) | H | OH |
| −CH₂−CH₂−(adamantyl) | H | OCH₃ |
| −CH₂−CH₂−(adamantyl) | H | OH |
| CH₃−CH−CH₂N(4-Ph-4-OAc-piperidinyl) | H | HO |
| CH₂CH₂N(4-Ph-4-OAc-piperidinyl) | H | HO |
| CH₂CH₂N(4-Ph-4-OC(O)Et-piperidinyl) | H | HO |
| CH₃−CH−CH₂N(4-Ph-4-OC(O)Et-piperidinyl) | H | HO |
| CH₂CH₂N(Me)₂ | H | HO |
| CH₃−CHCH₂N(Me)₂ | H | HO |
| CH₂CH₂N(Et)₂ | H | HO |
| CH₃−CHCH₂N(Et)₂ | H | HO |

-continued structure: R³ substituted benzazepine with CH₃ at position 1 and N—R

| R³ | R¹ | |
|---|---|---|
| CH₃O | (CH₃)₂C=CH—CH₂— | 3-(3,3-Dimethylallyl)-8-methoxy-1-methyl-1,2,4,5-tetrahydro-3H,3-benzazepine |
| HO | (CH₃)₂C=CH—CH₂— | 3-(3,3-Dimethylallyl)-8-hydroxy-1-methyl-1,2,4,5-tetrahydro-3H,3-benzazepine |
| CH₃O | ▷—CH₂ | 3-Cyclopropylmethyl-8-methoxy-1-methyl-1,2,4,5-tetrahydro-3H,3-benzazepine |
| HO | ▷—CH₂ | 3-Cyclopropylmethyl-8-hydroxy-1-methyl-1,2,4,5-tetrahydro-3H,3-benzazepine |
| CH₃O | CH₂—CH—CH₂— | 3-Allyl-8-methoxy-1-methyl-1,2,4,5-tetrahydro-3H,3-benzazepine |
| HO | CH₂—CH—CH₂— | 3-Allyl-8-hydroxy-1-methyl-1,2,4,5-tetrahydro-3H,3-benzazepine |
| CH₃O | C₆H₅—CH₂CH₂— | 8-Methoxy-1-methyl-3-phenethyl-1,2,4,5-tetrahydro-3H,3-benzazepine |
| HO | C₆H₅—CH₂CH₂— | 8-Hydroxy-1-methyl-3-phenethyl-1,2,4,5-tetrahydro-3H,3-benzazepine |

PHARMOLOGICAL ACTIVITY OF BENZAZEPINE COMPOUNDS

Compounds of the present invention have been evaluated in experimental animals for analgesic activity and ability to antagonize the action of strong narcotic analgesics. It has been possible through use of conventional testing methods in animals to demonstrate various degrees of these activities by one or several methods and routes of administration at dose levels which do not result in gross toxic manifestations. In addition, other pharmacological properties of representative compounds of this invention have been detected, such as antihistaminic and anticholinergic activity. Recognized indications of drug addiction typical of the opiates have not been observed following administration to morphine dependent monkeys indicating a lack of addiction liability for these benzazepine compounds. Thus, results of pharmacological evaluations support the contention that the benzazepine compounds of the formulae disclosed in this application are of value as narcotic antagonist analgesics.

Results

Analgesic Activity

Table I provides a summary of the results obtained when representative compounds of this invention were tested for analgesic activity by the methods described. The narcotic antagonist analgesic pentazocine and the narcotic analgesics morphine and codeine are included for comparison. It is evident from this comparison that the majority of compounds which exhibit significant activity at dose levels below those producing toxic manifestations, i.e. less than the highest nonsymptomatic dose (HNSD), are effective primarily by the parenteral route. Exceptions are compounds SR654-66A, SR727-52A, and SR701-77A which are active by the oral route. The predominance of parenteral efficacy is evident by both the hot plate method where the intraperitoneal route was used and by the writhing method with administration by the subcutaneous route. The most active compounds were SR751-227A and SR673-50A. In addition, these compounds also exhibit the greatest separation between effective dose and toxic or lethal doses indicating a more favorable therapeutic index.

The most active compounds listed in Table 1 are comparable to codeine by the hot plate method of testing and are 6 to 8 times more active than pentazocine by the intraperitoneal route in this test. Compound SR654-66A, which exhibits activity by the oral route in the writhing test, is approximately twice as active as pentazocine.

TABLE I

| | | Analgesic Acitivity of Benzazepine Compounds | | | | | | | |
|---|---|---|---|---|---|---|---|---|---|
| | | HNSD* mg/kg | | LDSO mg/kg | | Hot Plate ED50 mg/kg | | Writhing ED50 mg/kg | |
| Compound No. | Name | PO** | IP*** | PO | IP. | PO | IP | PO | SC**** |
| SR673-S0A | N-Phenethyl-7-methoxy-1,2,4,5 tetra-hydro-3H-3-benzazepine hydrochloride | 178 | 32 | >1000 | 50 | >178 | 12 | >178 | ~11 |
| SR654-66A | 3-cyclopropyl-methyl-1,2,4,5 tetrahydro-3H,3-benzazepine hydrochloride | 56 | 18 | 477 | 52 | 37 | 12 | 49 | >18 |
| SR727-51A | 3-Allyl-7-methoxy-1,2,4,5 | 178 | 56 | >1000 | 60 | >178 | 42 | >178 | >56 |

TABLE I-continued
Analgesic Acitivity of Benzazepine Compounds

| Compound No. | Name | HNSD* mg/kg PO** | HNSD* mg/kg IP*** | LD50 mg/kg PO | LD50 mg/kg IP. | Hot Plate ED50 mg/kg PO | Hot Plate ED50 mg/kg IP | Writhing ED50 mg/kg PO | Writhing ED50 mg/kg SC**** |
|---|---|---|---|---|---|---|---|---|---|
| | tetrahydro 3H,3-benzazepine hydrochloride | | | | | | | | |
| SR727-S2A | 7-Methoxy-3-(3-phenylallyl)-1,2,4,5-tetrahydro-3H,3-benzazepine hydrochloride | 100 | 18 | 316 | 26 | 125 | >18 | 120 | >18 |
| SR709-8A | 3-Ethyl-7-methoxy-1,2,4,5-tetrahydro-3H,3-benzazepine hydrochloride | 125 | 30 | 1000 | 44 | >125 | 15 | >125 | >32 |
| SR701-77A | 7-Methoxy-3-methyl-1,2,4,5-tetrahydro-3H,3-benzazepine hydrochloride | 180 | 32 | 700 | 83 | 140 | 20 | >180 | >32 |
| SR727-915A | 7-Methoxy-3-n-propyl-1,2,4,5-tetrahydro-3H,3-benzazepine hydrochloride | 316 | 32 | 686 | 50 | >316 | 26 | >316 | >32 |
| SR673-64A | 7-Hydroxy-3-phenyl-ethyl-1,2,4,5 tetra hydro-3H,3-benzazepine hydrochloride | 178 | 55 | >1000 | 140 | >178 | 26 | >178 | |
| SR701-67A | 3-Allyl-7-hydroxy-1,2,4,5-tetrahydro-3H,3-benzazepine hydrochloride | 316 | 50 | 700 | 125 | >316 | 35 | >316 | |
| SR751-227A | 7-Methoxy-3-[2-(4-phenyl-1-piperazinyl)-ethyl]-1,2,4,5-tetrahydro-3H,3-benzazepine dihydrochloride | 100 | 32 | ~300 | ~80 | ~80 | ~8 | >100 | |
| SR727-42A | 3-Cyclopentyl methyl-7-methoxy-1,2,4,5-tetrahydro-3H,3-benzazepine | 178 | 56 | 784 | 75 | >178 | 45 | >178 | |
| SR701-86 | 7-Hydroxy-3-(3-phenylallyl)-1,2,4,5-tetrahydro-3H,3-benzazepine | 1000 | 300 | >1000 | — | >1000 | 230 | 210 | |
| | Pentazocine | 316 | 316 | ~800 | >500 | >316 | 100 | 70 | |
| | Morphine | 56 | 10 | ~800 | 250 | 14 | 2.5 | 3 | |
| | Codeine | 100 | 32 | 540 | 104 | 20 | 12 | 17 | |

*HNSD = Highest Non Symptomatic Dose
**PO = Per Os
***IP = Intraperitoneal
****SC = Subcutaneous The benzazepine compounds listed in Table II are examples showing narcotic antagonist activity determined by two methods. Inhibition of oxymorphone mydriasis in the mouse provided qualitative evidence of antagonist activity whereas inhibition of morphine analgesis in the rat permitted semi-quantitative expression of antagonism. Narcotic antagonist activity was demonstrated for all of the benzazepine compounds in Table II by both of the test methods. Compounds SR701-37A appears to be a more potent antagonist than pentazocine whereas SR673-50A, SR727-52A and SR727-51A are about equipotent to pentazocine. In addition to therapeutic application of these compounds as analgesics, narcotic antagonists have been of value in treatment of narcotic addiction. Compounds having narcotic antagonist activity but no morphine-like activity (e.g. analgesia) may be of interest in treating narcotic (e.g. heroin) addiction and/or reversing the toxic manifestations of narcotic overdosage.

For all benzazepine compounds listed, various degrees of similar toxic manifestations occurred with increasing dosage characterized by depression, ataxia, reduced respiration, exophthalmos, salivation, lacrimation, vasodilation, cyanosis and mydriasis. Also common with all compounds was development of moderate to severe clonic convulsions and death of the animals was attributable to respiratory failure.

TABLE II
Narcotic Antagonist Activity of Benzazepine Compounds

| Name | Antagonism of Oxymorphone Mydriasis PO* | Antagonism of Oxymorphone Mydriasis IP** | Antagonism of Morphine Analgesia SC*** |
|---|---|---|---|
| 3-(3,3-dimethylallyl)-7-hydroxy-1,2,4,5 tetrahydro-3H,3-benzazepine hydrochloride (Compound No. SR701-37A) | + | + | +++ |
| N-Phenethyl-7-methoxy-1,2,4,5 tetrahydro-3H-3-benzazepine hydrochloride | + | + | + |
| 7-Methoxy-3-(3-phenylallyl)-1,2,4,5 tetrahydro-3H,3-benzazepine hydrochloride | + | + | + |
| 3-Allyl-7-methoxy-1,2,4,5-tetrahydro 3H,3-benzazepine hydrochloride | + | + | + |
| Pentazocine | + | + | + |
| Morphine | — | — | — |
| Codeine | — | — | — |
| Nalorphine | + | + | Approximately 20–100 times more active then compounds listed |

Antihistaminic and Anticholinergic Activity

Table III provides a summary of the relative antihistaminic and anticholinergic activity of benzazepine compounds, as demonstrated through use of isolated segments of guinea pig ileum. It is apparent from these results that positive antihistaminic action can be elicited with the compounds listed in the table. Weak anticholinergic activity relative to atropine was exhibited by these compounds.

TABLE II-continued
Narcotic Antagonist Activity of Benzazepine Compounds

| Name | Antagonism of Oxymorphone Mydriasis PO* IP** | Antagonism of Morphine Analgesia SC*** |
|---|---|---|
| | | above. |

*PO = Per OS
**IP = Intraperitoneal
***SC = Subcutaneous

TABLE III
Antihistamine and Anticholinergic Acitivity of Benzazepine Compounds

| Compound | Conc. for 50% block of Acetylcholine μg/20 ml | Conc. for 50% block of Histamine μg/20 ml |
|---|---|---|
| SR701-37A | 120 | 76 |
| SR727-43A* | 220 | 20 |
| SR701-89A** | >1000 | 75 |
| SR730-243A*** | 94 | 54 |
| SR654-66A | 540 | 20 |
| SR673-50A | 74 | 10 |
| Atropine | 0.0035 | 37 |
| Diphenhydramine | 3.3 | 0.12 |

*3-Cyclopropylmethyl-7-methoxy-1,2,4,5-tetrahydro-3H, 3-benzazepine
**7-Hydroxy-3-propyl-1,2,4,5-tetrahydro-3H,3-benzazepine
***7-Methoxy-3-(-1-methyl-2-phenethyl)-1,2,4,5-tetrahydro-3H,3-benzazepine

TABLE IV

| Compound of Example: | I.P.[1] Symptomatology HTD[2] mg/kg | I.P.[1] Symptomatology LD$_{50}$[3] mg/kg | PBQ[4] Analgesia P.O.[5] mg/kg | PBQ[4] Analgesia S.C.[6] mg/kg | MTS[7] S.C. | Local Anesthetic Sciatic Block 1% | Narcotic Antagonism I.P. |
|---|---|---|---|---|---|---|---|
| 1 | 3 | 60 | 60 | 10 | >3 | Positive | Negative |
| 2 | 10 | 200 | >100 | 100 | — | Positive | Negative |
| 3 | 30 | 50 | >30 | 20 | — | Positive | Negative |
| 4 | 30 | 96 | 100 | 20 | >56 | Positive | Positive |
| 5 | ~10 | ~200 | >100 | >30 | >30 | Positive | Positive |
| 6 | 10 | >300 | >100 | >100 | — | — | Positive |
| 7 | 40 | 100 | >100 | 50 | — | Positive | Negative |
| 8 | 20 | 30 | >200 | >30 | — | Positive | Positive |
| 9 | 20 | 80 | >100 | — | — | Positive | Negative |
| 11 | 20 | 50 | >100 | — | — | Positive | Positive |
| 13 | 30 | 80 | >100 | 30 | — | — | Negative |
| 14 | 60 | 80 | >300 | >100 | — | Positive | Positive |
| 18 | 25 | 80 | >200 | >30 | — | — | Negative |
| 20 | 1 | 60 | >100 | 80 | — | Positive | Negative |
| 21 | 30 | 80 | >200 | — | — | — | Positive |
| 22 | 30 | 50 | >300 | >30 | — | — | Positive |
| 23 | 20 | 50 | >100 | — | — | Positive | Positive |
| 24 | 30 | 50 | >200 | 10 | 5 | — | Positive |
| 28 | 20 | 60 | >100 | >30 | 10 | — | Positive |
| 30 | 1000 | >1000 | >600 | — | — | — | Negative |
| 31 | 30 | 80 | >100 | 7 | 20 | Positive | Negative |
| 32 | ~10 | ~60 | ~30 | ~15 | — | Positive | Negative |
| 33 | 1 | 50 | >100 | 20 | — | — | Negative |
| 34 | 10 | 60 | >100 | 20 | >40 | Positive | Positive |
| 36 | 10 | 60 | >100 | 6 | 10 | Insoluable | Negative |
| 37 | 10 | 60 | >30 | >20 | 10 | — | Negative |
| 38 | 10 | 200 | >100 | >100 | >10 | — | Positive |
| 39 | 10 | ≅150 | >100 | >30* | — | Positive | Negative |
| 40 | 30 | >100 | >100 | >30* | — | Positive | Negative |
| 41 | ~3 | ~60 | >30 | >30 | >30 | Positive | Negative |
| 42 | 10 | 60 | >100 | >30 | — | — | Negative |
| 44 | 10 | 60 | 30 | 10 | — | Insoluable | Negative |
| 48 | 30 | 60 | 80 | 50 | — | Positive | Some |
| 49 | 30 | 200 | >100 | 30 | — | Positive | Negative |
| 50 | 10 | 25 | >30 | >30 | — | Positive | Negative |
| 51 | 10 | ≅150 | >100 | ≅15 | — | Positive | Negative |
| 53 | 10 | ≅65 | >100 | >10 | — | Positive | Negative |
| 54 | 3 | 60 | >100 | 30 | — | Positive | Negative |
| 55 | 10 | ≅150 | >100 | >30 | — | Positive | Pos.@ 100, 30 and 10 mg/kg |
| 56 | 10 | ≅65 | >100 | >30 | — | Positive | Negative |
| 57 | 10 | >100 | >100 | >10 | — | Positive | Pos.@ 100 mg/kg |
| 58 | 1 | >300 | >30 | ≅2 | — | Insoluble | Negative |
| 59 | 0.3 | ≅60 | >30 | >1 | — | Insoluble | Negative |
| 60 | 10 | ≅200 | >100 | >30 | — | Positive | Negative |
| 61 | 3 | ≅60 | >30 | ≅20 | — | Positive | Negative |
| 62 | 10 | ≅200 | >100 | >30 | — | Positive | Negative |

TABLE IV-continued

| Compound of Example: | I.P.[1] Symptomatology | | PBQ[4] Analgesia | | MTS[7] | Local Anesthetic Sciatic Block | Narcotic Antagonism |
| --- | --- | --- | --- | --- | --- | --- | --- |
| | HTD[2] mg/kg | LD$_{50}$[3] mg/kg | P.O.[5] mg/kg | S.C.[6] mg/kg | S.C. | 1% | I.P. |
| 63 | 3 | ≅60 | >30 | >3 | — | Positive | Negative |

[1] IP = intraperitoneal route
[2] HTD = highest tolerated dose
[3] LD$_{50}$ = median lethal dose
[4] PBQ = phenylbenzoquinone writhing
[5] PO = oral route
[6] SC = subcutaneous route
[7] MTS = mouse tail stimulation
*Median effective dose

I claim:
1. A compound of the formula

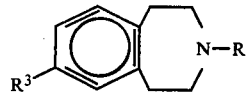

wherein R is cycloalkylmethyl of 4 to 6 carbons and R$^3$ is hydroxy or methoxy.

2. The compound of claim 1, 3-cyclopropylmethyl-7-hydroxy-1,2,4,5-tetrahydro-3H3-benzazepine.

* * * * *